United States Patent [19]
Tregear et al.

[11] Patent Number: 6,013,434
[45] Date of Patent: *Jan. 11, 2000

[54] OLIGONUCLEOTIDE-POLYAMIDE CONJUGATES

[75] Inventors: Geoffrey William Tregear, Hawthorn; Jim Haralambidis, Richmond, both of Australia

[73] Assignee: Howard Florey Institute of Experimental Physiology and Medicine, Parkville, Australia

[ * ] Notice: This patent is subject to a terminal disclaimer.

[21] Appl. No.: 08/343,535
[22] PCT Filed: May 28, 1993
[86] PCT No.: PCT/AU93/00252
  § 371 Date: Feb. 9, 1995
  § 102(e) Date: Feb. 9, 1995
[87] PCT Pub. No.: WO93/24511
  PCT Pub. Date: Dec. 9, 1993

Related U.S. Application Data

[63] Continuation-in-part of application No. 08/068,604, May 27, 1993, Pat. No. 5,552,540, which is a continuation of application No. 07/457,747, Dec. 22, 1989, abandoned.

[30] Foreign Application Priority Data

May 29, 1992 [AU] Australia ................................. PL2682

[51] Int. Cl.[7] ....................................................... C12Q 1/68
[52] U.S. Cl. ............................. 435/6; 536/26.6; 536/28.4
[58] Field of Search ................................. 536/26.6, 28.54, 536/28.55, 28.4, 28.5; 435/6

[56] References Cited

U.S. PATENT DOCUMENTS 5,427,914 6/1995 Dennis ..................................... 435/7.23

FOREIGN PATENT DOCUMENTS

WO 88/10264 12/1988 WIPO.
92/05186 4/1992 WIPO.

*Primary Examiner*—Scott W. Houtteman
*Attorney, Agent, or Firm*—Sughrue, Mion, Zinn, Macpeak & Seas, PLLC

[57] ABSTRACT

This invention relates to novel oligonucleotide-polyamide conjugates preferably having a free 3' hydroxl moiety, and wherein the polyamide is coupled to the oglionucleotide through its carboxyl terminus. A nucleotide polymer conjugate of the formula (I): Nu—NUC—C≡C—$X^1$—NH—$X^2$—$X^3$ where $X^1$ is an unsubstituted or substituted $C_1$–$C_{10}$ alkylene group, in which one or more carbons may optionally be replaced by —NH—, —O— or —S—; $X^2$ is a bond, or an unsubstituted or substituted $C_1$–$C_{20}$ alkylene group, in which one or more carbons may optionally be replaced by —NH—, —O— or —S—; the optional substituents in $X^1$ or $X^2$ are selected from a variety of groups; $X^3$ is an amino acid or a polyamide linked via its carboxy terminus; NUC is a nucleoside group of any one of formulas (a), (b), (c), (d) where→indicates the bond to the —C—C— group in formula (I), and $X^4$ is a sugar group of formula(e) where the 5' oxygen is linked to Nu, and $X^5$ and $X^6$ are each independently H or OR, where R is H, a protecting group, or a solid phase matrix, and Nu is an oligonucleotide. Methods of preparing these compounds, and various uses, for example, as PCR primers, or as a substrate for DNA or RNA polymerase, are also disclosed.

19 Claims, 6 Drawing Sheets

B = Adenyl, Guanyl, Thyminyl or Cytosinyl (1) 90% TFA / ethanedithiol or 3% DCA / DCM
(2) FmocNH(CH$_2$)$_5$CO$_2$Pfp / HOBT
(3) 4,4'-dimethoxytrityl chloride Dmt = 4,4'-dimethoxytrityl group

20

(1) 20% piperidine / DMF.
(2) Fmoc-Lys(Biotin)-OPfp / HOBT.
(3) 20% piperidine / DMF.
(4) Fmoc-Ala-OPfp / HOBT.
(5) 20% piperidine / DMF.
(6) Ac$_2$O / DMAP, pyridine.
(7) 3% DCA / DCM.
(8) DNA synthesis, cleavage and deprotection.

5

OLIGONUCLEOTIDE-POLYAMIDE CONJUGATES

This application is a national stage of PCI/AU93/00252 filed May 28, 1993 and a continuation-in-part of application Ser. No. 08/068,604 filed May 27, 1993, now U.S. Pat. No. 5,552,540 which is a continuation of application Ser. No. 07/457,747 filed Dec. 22, 1989 (abandoned).

TECHNICAL FIELD

This invention relates to novel oligonucleotide-polyamide conjugates preferably having a free 3' hydroxyl moiety, and wherein the polyamide is coupled to the oligonucleotide through its carboxyl terminus.

BACKGROUND ART

A number of molecular biological methods involve the detection of nucleotide sequences, or the tagging of nucleotide sequences with reporter groups. For example, the widely utilised polymerase chain reaction technique (PCR) allows many copies of a desired DNA to be generated from only a few target molecules within a period of 1 to 2 hours and consequently has found applications of nucleic acid detection techniques previously limited by low sensitivity. Detection of amplified PCR products may be carried out in a number of ways. It is most desirable to be able to detect amplification products non-radioactively, for example, using a reporter group within the amplified nucleotide sequences.

Similarly, in reactions such as nick translation, it is desirable to incorporate a labelled nucleotide into reaction products produced by DNA polymerase or RNA polymerase for subsequent detection of hybridisation products.

DISCLOSURE OF INVENTION

In accordance with the present invention there is provided in one aspect a nucleotide polyamide conjugate of the formula (I):

$$Nu-NUC-C\equiv C-X^1-NH-X^2-X^3 \qquad (1)$$

where, $X^1$ is an unsubstituted or substituted $C_1$–$C_{10}$ alkylene group, in which one or more carbons may optionally be replaced by —NH—, —O— or —S—, $X^2$ is a bond, or an unsubstituted or substituted $C_1$–$C_{20}$ alkylene group, in which one or more carbons may optionally be replaced by —NH—, —O— or —S—, the optional substituents in $X^1$ or X2 selected from one or more of: oxo, amino, thioxo, hydroxyl, mercapto, carboxyl, halogen, lower alkyl, phenyl, amino-lower alkyl, ester-lower alkyl, amido-lower alkyl, ether-lower alkyl, or thioether-lower alkyl, groups, the sulfur analogues of these substituents, or the side-chain substituents from naturally occurring amino acids, and the closely related analogues of these sidechains, for example. $X^3$ is an amino acid, or a polyamide linked via its carboxy terminus, NUC is a nucleoside of any one of the formulas:

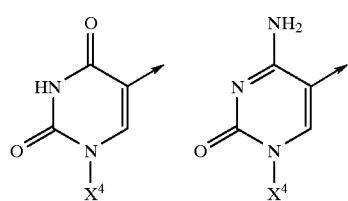

-continued

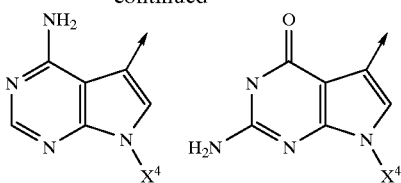

where →indicates the bond to the —C≡C— group in formula (I), and $X^4$ is a sugar group of the formula:

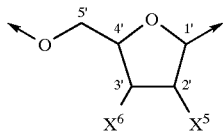

where the 5' oxygen is linked to Nu, and $X^5$ and $X^6$ are each independently, H or OR, where R is H, a protecting group, or a solid phase matrix, and Nu is an oligonucleotide.

$X^1$ is an unsubstituted or substituted $C_1$–$C_{10}$ alkylene group, in which one or more carbons may optionally be replaced by —NH—, —O— or —S—, and the optional substituents in $X^1$ are selected from one or more of oxo, amino, thioxo, hydroxyl, mercapto, carboxyl, halogen, lower alkyl, phenyl, amino-lower alkyl, ester-lower alkyl, amido-lower alkyl, ether-lower alkyl, or thioether-lower alkyl, groups, and the like, such as the sulfur analogues of these compounds, and any other functional groups. Other possible substituents are the side-chain substituents from naturally occurring amino acids, and their closely related analogues, for example. Preferably, the $C_1$ to $C_{10}$ alkylene is $C_{1-3}$ alkylene and is optionally substituted with one or more of amide, halogen, aryl, ester and the like. A preferred form of $X^1$ is methylene.

$X^2$ is a bond, or an unsubstituted or substituted $C_1$–$C_{20}$ alkylene group, in which one or more carbons may optionally be replaced by —NH—, —O— or —S—, and the optional substituents in $X^2$ are selected from one or more of oxo, amino, thioxo, hydroxyl, mercapto, carboxyl, halogen, lower alkyl, phenyl, amino-lower alkyl, ester-lower alkyl, amido-lower alkyl, ether-lower alkyl, or thioether-lower alkyl, groups, the sulfur analogues of these substituents, or the side-chain substituents attached to the α-carbon of naturally occuring amino acids, and their similar analogues, for example. $X^2$ preferably has the form —CO—($C_1$ to $C_9$ alkylene)—NH—, where the alkylene may be further substituted, for example with substituents attached to naturally occurring amino acids, or the like. A preferred form of $X^2$ is —CO—$(CH_2)_5$—NH—, or the like.

The polyamide ($X^3$) is preferably a polypeptide comprising two or more amino acids. Preferably, the polyamide also contains one or more reporter groups. Alternatively, the polyamide may comprise a single amino acid.

The nucleoside group NUC in one preferred form has the structure:

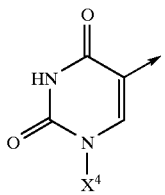

where $X^4$ is as described before. In the sugar moiety, $X^4$, substituents $X^5$ and $X^6$ are each independently, H or OR, where R is H, a protecting group, or a solid phase matrix, and preferably $R^5$ is H, and $R^6$ is OR, where R is H or a support matrix.

Particularly preferred compounds of this invention comprise compounds of the formula (II):

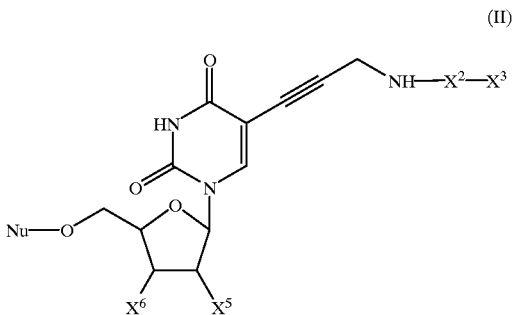

(II)

wherein $X^2$, $X^3$, $X^5$, $X^6$ and Nu are as previously described.

The group $X^3$ represents a polyamide which is linked covalently to the group $X^2$. The polyamide may be formed from naturally occurring amino acids (Biochemistry, 2nd Edition, Albert L. Lehninger, pp. 72–77, 1970), such as lysine, valine, glycine, serine, threonine, tyrosine, methionine, proline, etc. linked through amide or so-called peptide bonds. Alternatively, the polyamide may be formed from synthetic amino acids, synthetic amino acids being those amino acids which do not occur naturally in proteins, or else the polyamide may be a combination of natural and synthetic amino acids. Preferably, the synthetic amino acids may comprise α,ω-amino-carboxylic acids which may be represented by the general formula $H_2NCHR^1COOH$, where $R^1$ is any organic moiety such as $C_{1-20}$ alkylene which may be straight- or branch-chained, either saturated, or unsaturated by having one or more olefinic or acetylinic C—C bonds for example, cycloalkyl, which may be saturated or partially saturated and/or interrupted by one or more hetero atoms or groups containing such hetero atoms such as amide groups and/or substituted with halogen, cyano, amino or unsubstituted or substituted phenyl or benzyl, as just some examples. The polyamide may contain any number of amino acid units (residues) for example from 1 to 100 amino acids.

The polyamide $(X^3)$ may form a peptide comprising naturally or non-naturally occurring amino acids. The sequence of the peptide can be designed to suit any desired application, such as interaction with antibodies, enzymic reactions and the like.

The polyamide may contain one or more reporter groups attached to the polyamide chain via a derivatised amino acid such as lysine. Reporter groups may comprise fluorescent moieties, chemiluminescent moieties, paramagnetic moieties and the like, biotin and colloidal compounds such as ferritin or colloidal silver or gold and enzymes. Reporter groups may be covalently linked one or more amino acids within the polyamide, particularly through the free amino group of lysine.

Fluorophore reporter groups may be selected from: fluorescein-5-isothiocyanate, diacyl (such as isobutyryl, acetyl or pivaloyl) fluorescein-5 and/or 6 carboxylic acid pentafluorophenyl ester, 6-(diacyl-5 and/or 6-carboxamide-fluorescein)amino-hexanoic acid pentafluorophenyl ester, Texas Red (Trademark of Molecular Probes, Inc.), tetramethylrhodamine-5 (and 6) isothiocyanate, oesin-isothiocyanate, erythrosin-5-isothiocyanate, 4-chloro-7-nitrobenz-2-oxa-1,3-diazole, 4-fluoro-7-nitrobenz-2-oxa-1, 3-diazone, 3-(7-nitrobenz-2-oxa-1,3-diazol-4-yl) methylamino-propionitrile, 6-(7-nitrobenz-2-oxa-1,3-diazol-4-yl)aminohexanoic acid, succinimidyl 12-(N-methyl-N-(7-nitrobenz-2-oxa-1,3-diazol-4-71) aminododecanoate, 7-diethylamino-3-(4'-isothio-cyanatophenyl)-4-methylcoumarin (CP), 7-hydroxycoumarin-4-acetic acid, 7-dimethylamino-coumarin-4-acetic acid, succinimidyl 7-dimethylaminocoumarin-4-acetate, 7-methoxycoumarin-4-acetic acid, 4-acetamide-4'-isothiocyanatostilbene-2-2'-disulfonic acid (SITS), 9-chloroacridine, succinimidyl 3-(9-carbazole)-propionate, succinimidyl 1-pyrenebutyrate, succinimidyl 1-pyrenenonanoate, p-nitrophenyl 1-pyrenebutyrate, 9-anthracenepropionic acid, succinimidyl anthracene-9-propionate, 2-anthracenesulfonyl chloride; or fluorophore precursors, which when treated in a particular manner fluoresce.

Reporter groups may be attached to polyamides according to conventional techniques known per se in the art. For example, nucleophilic groups on polyamides such as primary amine groups may react with the fluorescent or enzymic reporter groups to form a covalent bond therebetween. Alternatively, bifunctional coupling reagents known per se in the art (for example as described in the Pierce Chemical Company catalogue, 1987) may be employed to attach reporter groups to polyamides Biotin may be incorporated into the polyamide by conventional methods. For example, underivatised biotin may be incorporated into a polyamide utilising the BOP coupling method (Castro, B, et al., Synthesis (1976) pp. 751–752). Alternatively, biotin can be introduced as the N-hydroxysuccinimidyl active ester. It may also be incorporated by using a biotinylated amino acid derivative, for instance. Biotin may be detected using avidin attached to a reporter group. For example, streptavidin-alkaline phosphatase conjugate may be employed to bind to biotin. The alkaline phosphatase can react with a suitable substrate to generate an insoluble diprecipitate which can be detected visually.

Enzymic reporter groups may be selected from β-galactosidase, horse radish peroxidase, urease, alkaline phosphatase, dehydrogenases, luciferase and carbonic anhydrase. Generally, enzymes will react with one or more substrates to produce a detectable signal such as a colour change, luminescence or formation of a precipitate.

The number of reporter groups which may be included in the polyamide is unimportant to this invention, and for example, from 1 to 20 or more reporter groups may be incorporated into the polyamide. The positioning of the reporter groups within the polyamide is not important to this invention. For example, a single reporter group may be present at the terminal end of the polyamide distal to the alkyne amino group. Alternatively, a reporter group may be proximal to the alkyne amino group. As a further alternative, multiple reporter groups may be distributed along the length of the polyamide.

The oligonuceotide Nu is any suitable nucleotide sequence, but in one preferred form has the general formula:

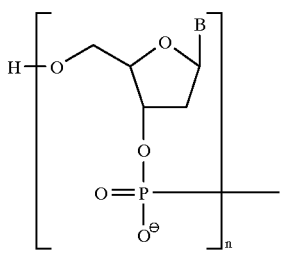

where B is independently selected from adenyl, guanyl, thyminyl or cytosinyl, and n is from 1 to about 400, or more preferably from 2 to about 200.

The oligonucleotide sequence Nu which extends from the 5' hydroxyl moiety of the sugar residue compounds of the formulae I and II may be of any desired nucleotide sequence and composition which allows hybridisation to a DNA or RNA target and further is capable of acting as a primer for DNA or RNA polymerase. The oligonucleotide may be comprised of deoxyribonucleotides, ribonucleotides or a combination of deoxy and ribonucleotides. The oligonucleotide may comprise from 1 to 400 nucleotides or more, preferably 2 to 200 nucleotides. The oligonucleotides may be suitably modified to increase half-life in-vivo without effecting hybridisation. For example, the oligonucleotide may be modified by replacing 1 or more of the non-bridging oxygens on the phosphorous backbone with sulphur or amines, according to the procedures of Argawal et al. (*Proc. Nail. A cad. Sci. USA* 85 (1988), pp. 7079–7083) or Stein and Cohen, (*Cancer. Res.* 48 (1988), pp. 2659–2688). Such modified oligonucleotides are within the scope of the term oligonucleotide. The term "oligonucleotide" may also include a single nucleotide (ribo or deoxyribonucleotide) or a polynucleotide comprises of ribonucleotides, deoxyribonucleotides or mixtures thereof.

The general process for preparing a nucleotide polymer conjugate of the formula (I)

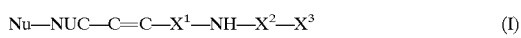

where, the substituents are as described above, involves a process comprising: (1) providing a compound of the formula (III):

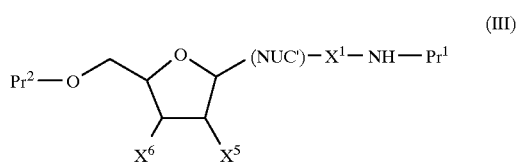

in which, NUC' is a group having any one of the formulas:

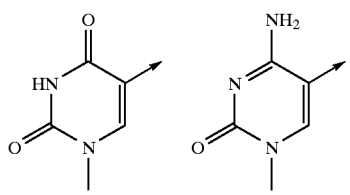

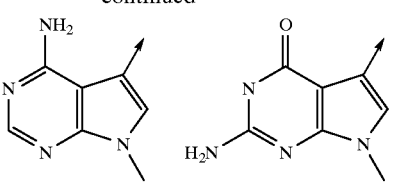

and $X^1$, $X^5$, and $X^6$ are as previously described, and $Pr^1$ and $Pr^2$ are protecting groups which may be the same or different; (2) deprotecting the pendant amino group by removing $Pr^1$ in compound (III) under conditions which may or may not remove $Pr^2$ and thereafter reacting the deprotected compound with a compound of the formula $Pr^3X^2R^x$ wherein $X^2$ is as previously described, $Pr^3$ is a protecting group and $R^x$ is a leaving group, so as to covalently link $X^2$ to the pendant amino group, to give:

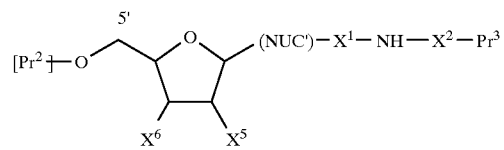

and in the case where the 5'-OH group is free this group is optionally reprotected with $Pr^2$ a removable protecting group, the same or different to $Pr^2$ in step (1), or when $X^2$ is a bond omitting step (2);

(3) deprotecting the pendant amino group by removing $Pr^3$ (or $Pr^1$ when $X^1$ is a bond) in the compound of step (2) and reacting it with an activated amino acid or polyamide, to introduce all or part of $X^3$, and if only part of $X^3$ has been introduced, thereafter sequentially adding one or more activated amino acids or polyamides one or more times under standard peptide synthesis conditions to add the remainder of $X^3$ to the compound, to form:

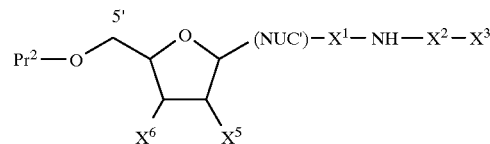

(4) deprotecting the 5'-OH group of the sugar moiety of the compound of step (3) if not previously deprotected and reacting the deprotected OH group with an activated nucleotide or oligonucleotide to form a 5'–3' bond, and thereafter sequentially adding one or more activated nucleotides to form an oligonucleotide chain, to add Nu to the compound; and (5) optionally removing any remaining protecting groups, and optionally cleaving said compound from a solid phase matrix where $X^5$ or $X^6$ is OR and R is a solid phase matrix, to give compound (I).

Amino and hydroxy groups on compounds of the formulae I and II may be protected with suitable protecting groups such as described by Green (*Protecting Groups in Organic Synthesis,* John Wiley & Sons, Inc., 1981). For example, hydroxy protecting groups may be selected from acyl such as substituted or unsubstituted alkanoyl (e.g. formyl, acetyl, propionyl, butyryl, isobutyryl, valeryl, bromoacetyl, dichloroacetyl, trifluoroacetyl), substituted or unsubstituted aroyl (e.g. benzoyl, toluoyl, xyloyl, nitrobenzoyl, bromobenzoyl, salicyloyl), arylalkyl (e.g. benyl), methyl, methoxy, methylthiomethyl, 2-methoxyethoxymethyl,bis(2- chloroethoxy)methyl,tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl 2-(phenylselenyl)ethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo) anthryl (Tritylone), dimethoxy trityl or pixyl, trimethylsilyl, isopropyldimethylsilyl, t-butyldimethylsilyl, triisopropylsilyl. Amino protecting groups may be selected from acyl, particularly organic acyl, for example, substituted or unsubstituted aliphatic hydrocarbonoxycarbonyl such as alkoxycarbonyl (e.g. methoxycarbonyl, ethoxycarbonyl, propoxycarbonyl, butoxycarbonyl, t-butyloxy-carbonyl. 5-pentoxycarbonyl); haloalkoxycarbonyl (e.g. chloromethoxy-carbonyl tribromoethoxycarbonyl, trichloroethoxycarbonyl); an alkane- or arenesulfonylalkoxy-carbonyl (e.g. 2-(mesyl)ethoxycarbonyl, 2-(p-toluenesulonyl)-ethoxycarbonyl); an alkylthioorarylthioalkoxycarbonyl(e.g.2-(ethylthio)ethoxycarbonyl, 2-(p-tolylthio)-ethoxycarbonyl), substituted or unsubstituted alkanoyl such as halo(lower)alkanoyl (e.g. formyl, trifluoroacetyl); a monocyclic or fused cyclic-alicyclic oxycarbonyl (e.g. cyclohexyloxycarbonyl, adamantyloxycarbonyl, isobomyloxycarbonyl); substituted or unsubstituted alkenyloxycarbonyl (e.g. allyoxycarbonyl); substituted or unsubstituted alkynyloxycarbonyl (e.g. 1,1-dimethylproparglyoxycarbonyl); substituted or unsubstituted aryloxycarbonyl (e.g. phenoxycarbonyl, p-methylphenoxycarbonyl); substituted or unsubstituted aralkoxycarbonyl (e.g. benyloxycarbonyl, p-nitrobenzyloxycarbonyl, p-phenylazobenzyloxycarbonyl, p-(p-methoxyphenylazo)-benzyloxycarbonyl, p-chlorobenzyloxycarbonyl, p-bromobenzyloxycarbonyl, α-naphthylmehoxycarbonyl, p-biphenylisopropoxycarbonyl, fluorenymethoxycarbonyl); substituted or unsubstituted arenesulfonyl (e.g. benzenesulfonyl, p-toluenesulfonyl);substituted or unsubstituted dialkylphosphoryl (e.g. dimethylphosphoryl); substituted or unsubstituted diaralkylphosphoryl (e.g. O,O-dibenzylphosphoryl); substituted or unsubstituted aryloxyalkanoyl (e.g. phenoxyacetyl, p-chlorophenoxyacetyl, 2-nitrophenoxyacetyl, 2-methyl-2-(2-nitrophenoxy)propyonyl); substituted or unsubstituted aryl such as phenyl, tolyl; or substituted or unsubstituted aralkyl such as benzyl, diphenylmethyl, trityl or nitrobenzyl.

Particularly preferred protecting groups are 4,4'-dimethoxytrityl, Fmoc, BOC and Pixyl.

The above protecting groups may comprise $Pr^1$ and $Pr^2$ (or $Pr^3$) as referred to hereinafter The above protecting groups may also be used to protect $X^5$ or $X^6$.

Compounds of the formulae I and II may be utilised to extend a template nucleotide sequence utilising DNA polymerase, such as the Klenow fragment or RNA polymerase (such as SP6 or T7 polymerase). In particularly, but in no way limiting this invention, the compounds of the formulae I and II may be utilised in the polymerase chain reaction (PCR) where the nucleotide sequence of the group Nu is selected to be complementary to a portion of a target sequence. Annealing of selected oligonucleotide "primers" to complementary sequences on opposite strands of a target DNA at low temperature followed by extension in a 3' direction by a thermo stable polymerase results in gene amplification. The amplified products can be readily detected by virtue of reporter groups containing within the polyamide residue. For example, fluorescent reporter groups may be detected by irradiating the amplified products with a light source within the excitation frequency of the fluorophore. Biotin containing reporter groups may be detected by reaction with avidin.

Compounds of this invention may be attached to a support matrix via the groups $X^5$ or $X^6$. The support matrix may, for example, be selected from controlled pore glass, such as aminopropyl controlled pore glass (AP-CPG) or polystyrene resins.

The compounds of this invention may be fully protected utilising protecting groups as described herein and attached to a support matrix, in a protected form but detached from a support matrix, or in a fully deprotected form.

Compounds of the formula II

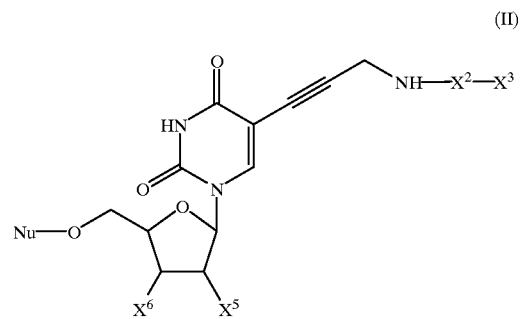

(II)

where $X^2$, $X^3$, $X^5$, $X^6$ and Nu are as defined previously, may be prepared generally by:

(1) providing a compound of the formula (IIIa):

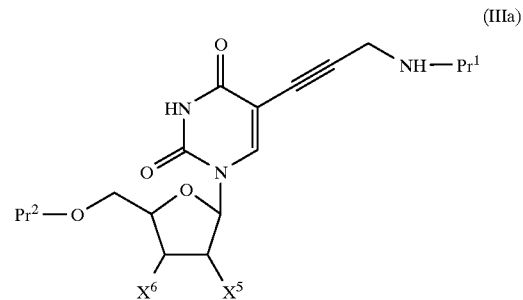

(IIIa)

in which $X^5$ and $X^6$ are as previously described, and $Pr^1$ and $Pr^2$ are protecting groups which may be the same or different;

(2) deprotecting the pendant amino group by removing $Pr^1$ in compound (IIa) under conditions which may or may not remove $Pr^2$ and thereafter reacting the deprotected compound with an amino acid of the formula $Pr^3X^2R^x$ wherein $X^2$ is as previously described, $Pr^3$ is a protecting group and $R^x$ is a leaving group, so as to covalently link $X^2$ to the pendant amino group, and in the case where the 5'-OH group is free this group is optionally reprotected with a removable protecting group which may be the same or different to the protecting group $Pr^2$ in step (1), or when $X^2$ is a bond omitting step (2); (3) deprotecting the pendent amino group by removing $Pr^3$ (or $Pr^1$ when $X^2$ is a bond) in the compound of step (2) and reacting it with an activated amino acid or polyamide, to introduce all or part of $X^3$, and if only part of $X^3$ has been introduced, thereafter sequentially adding one or more activated amino acids or polyamides one or more times under standard peptide synthesis conditions to add the remainder of $X^3$ to the compound; (4) deprotecting the 5'-OH group of the sugar moiety of the compound of step (3) if not previously deprotected, and reacting the deprotected OH group with an activated nucleotide or oligonucleotide to form a 5'–3' bond, and thereafter sequentially adding one or more activated nucleotides to form an oligonucleotide chain, to add Nu to the compound; and (5) optionally removing any remaining protecting groups, and optionally cleaving said compound from solid phase matrix where $X^5$ or $X^6$ is OR and R is a solid phase matrix, to give compound (II).

In the synthesis of compounds of the formula I and II where $X^2$ is a bond, step (2) comprises deprotecting the pendant amino group, with optional deprotection of the 5'OH group, and reacting the deprotected amino group with $X^2$ and then with $X^3$, as described above, each of which may be, for instance, an activated amino acid or peptide so as to covalently link the amino acid to the pendant amino group, without addition to the protected or deprotected 5'OH group of compounds of the formula (III); and in the case where the 5'OH group of compounds of the formula (III) is free this group is optionally reprotected with a removable protecting group.

Polyamides $X^3$ may, for example, be synthesised using solid phase Fmoc (Atherton, R. and Sheppard, R. C. (1985) *J Chem. Soc. Commun.*, pp. 165–166) or solid phase Boc (Barany, G. and Merrifield, R. B. (1980) *Solid-Phase Peptide Synthesis in "The Peptides"*, Vol. 2, E. Gross & J. Meienhofer Eds., Academic Press, New York, pp. 1–284) methodologies. In these methods, the amino acids are protected with standard protecting groups known per se in the art (for example, Green (1981) *Protective Groups in Organic Synthesis*, John Wiley & Sons, Inc.; Atherton and Sheppard (1985) *J. Chem. Soc. Commun.*, pp. 165–166; Barany and Merrifield, Supra) to protect reactive moieties.

Oligonucleotides Nu may be synthesized by the solid phase phosphotriester method (Sproat and Gait (1984) *Oligonucleotide Synthesis, A Practical Approach*, pp. 83–116, IRL Press, Oxford), solid phase H-phosphonate method (Froehler et al. (1986) *Nucleic Acids Research* 14, pp. 5399–5407) or the solid phase phosphoramidite method (Beaucage and Caruthers (1981) *Tetrahedron Let.*, 22, pp. 1859–1862). In each of these methodologies, reactive groups such as hydroxy or amino groups may be protected with standard hydroxy and amino protecting groups as described by (Green (1981) *Protective Groups in Organic Synthesis*, John Wiley & Sons, Inc.; Beaucage, S. L. and Caruthers, M. H. (1981) *Tetrahedron Lett.*, 22, pp. 1859–1862; Sproat, S. and Gait, M. J. (1984) *Oligonucleotide Synthesis, A Practical Approach*, pp. 83–116, IRL Press, Oxford).

Preferably, one of the groups $X^5$ or $X^6$ of compounds of the formula III is attached to a solid phase matrix. Most preferably the group $X^6$ is coupled to a solid phase matrix. The matrix may be activated to include suitable reactive groups as previously described. One or more reporter groups may be introduced into the polyamide at a number of different stages. The reporter group can be present in the amino acids prior to polyamide synthesis (step 3); introduced after polyamide synthesis (step 4); after oligonucleotide synthesis (step 5); or after deprotection and purification of the oligonucleotide-polyamide conjugate. The method chosen will depend upon the choice of reporter groups and synthetic procedure.

If the reporter group is stable to the conditions of both peptide and oligonucleotide synthesis, it can be incorporated from the start of polyamide synthesis, as a derivatized amino acid. If it is stable to the conditions of DNA synthesis but not those of peptide synthesis, it can be incorporated after the polyamide has been synthesized. If the reporter group is not stable to either peptide or oligonucleotide chain assembly, but is stable to deprotection methods, it can be incorporated after oligonucleotide chain assembly of the fully protected polyamide-oligonucleotide conjugate. If the label is not stable to any of the conditions used in the synthesis of the compounds of the invention, it may be introduced in a solution phase reaction with the purified fully deprotected polyamide-oligonucleotide conjugate.

Fluorophores may be introduced into the oligonucleotide-polyamide conjugate at any of steps (3) to (6). This is also the case for biotin.

Enzymes, and colloidal compounds such as colloidal gold, colloidal silver, ferritin, or biotin may be introduced at steps (3) to (6).

The polyamide portion of the oligonucteotide-polyamide conjugate may contain multiple reporter groups which may increase the detectable signal produced therefore facilitating detection.

The polyamide portion of the conjugate not only functions as a vehicle for attaching a reporter group, but may also act as an address marker to target a polyamide to a particular cell type, cellular location, or enhance the passage of an oligonucleotide through a cellular membrane. The address label activity of peptide sequences is well established (Verner and Schatz (1988) *Science* 241, pp. 1307–1313; and Goldfarb et al. (1986) *Nature* 322, pp.641–644). By selecting a peptide sequence which is, for example, recognised by a cell surface receptor, oligonucleotides conjugated to that peptide sequence may be transported into specific cell types where they can exert a biological effect, such as, in the case of anti-sense oligonucleotides, blocking transcription of viral or cellular RNA.

In a particularly preferred method of this invention, a compound of the formula (IIIa):

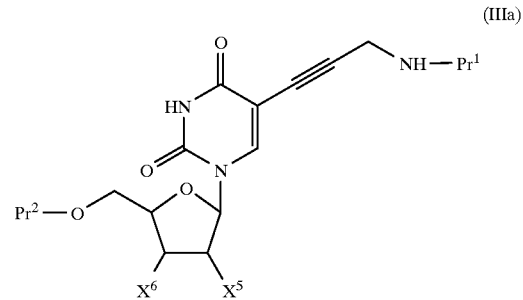

(IIIa)

wherein $Pr^1$, $Pr^2$, $X^5$ and $X^6$ are as previously described; is attached to a solid support by the 3'-hydroxyl group (ie, $X^6$ is OR, and R is a solid phase matrix); a spacer of the formula $Pr^3HNX^2COR^x$ or amino acid is added to the deprotected pendant amino group as described above, followed by addition of a polyamide chain by the sequential addition of one or more amino acid groups according to conventional peptide synthetic techniques.

An oligonucleotide chain is then added to the deprotected 5'-hydroxy group of the compounds of the formula IV. The various protecting groups $Pr^1$, $Pr^2$ and $Pr^3$ may be the same or different and are as previously described.

MODES FOR CARRYING OUT THE INVENTION

Figure 1:
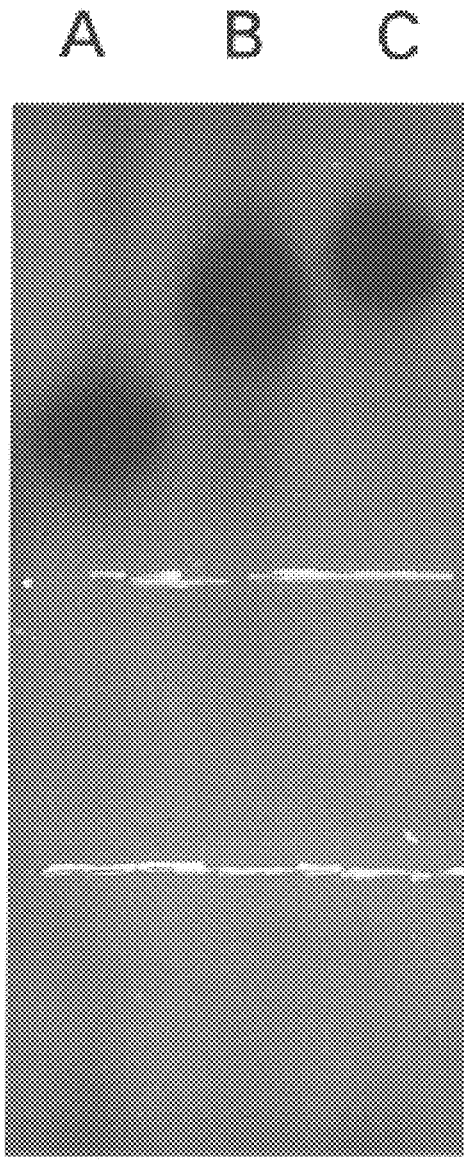
FIG. 1 herewith shows PAGE of 5'-end labelled oligonucleotides. Lanes A and C have normal oligonucleotides and lane B the 23 mer conjugate containing an Ahx-Lys (Biotin)-Ala peptide.
Figure 2:
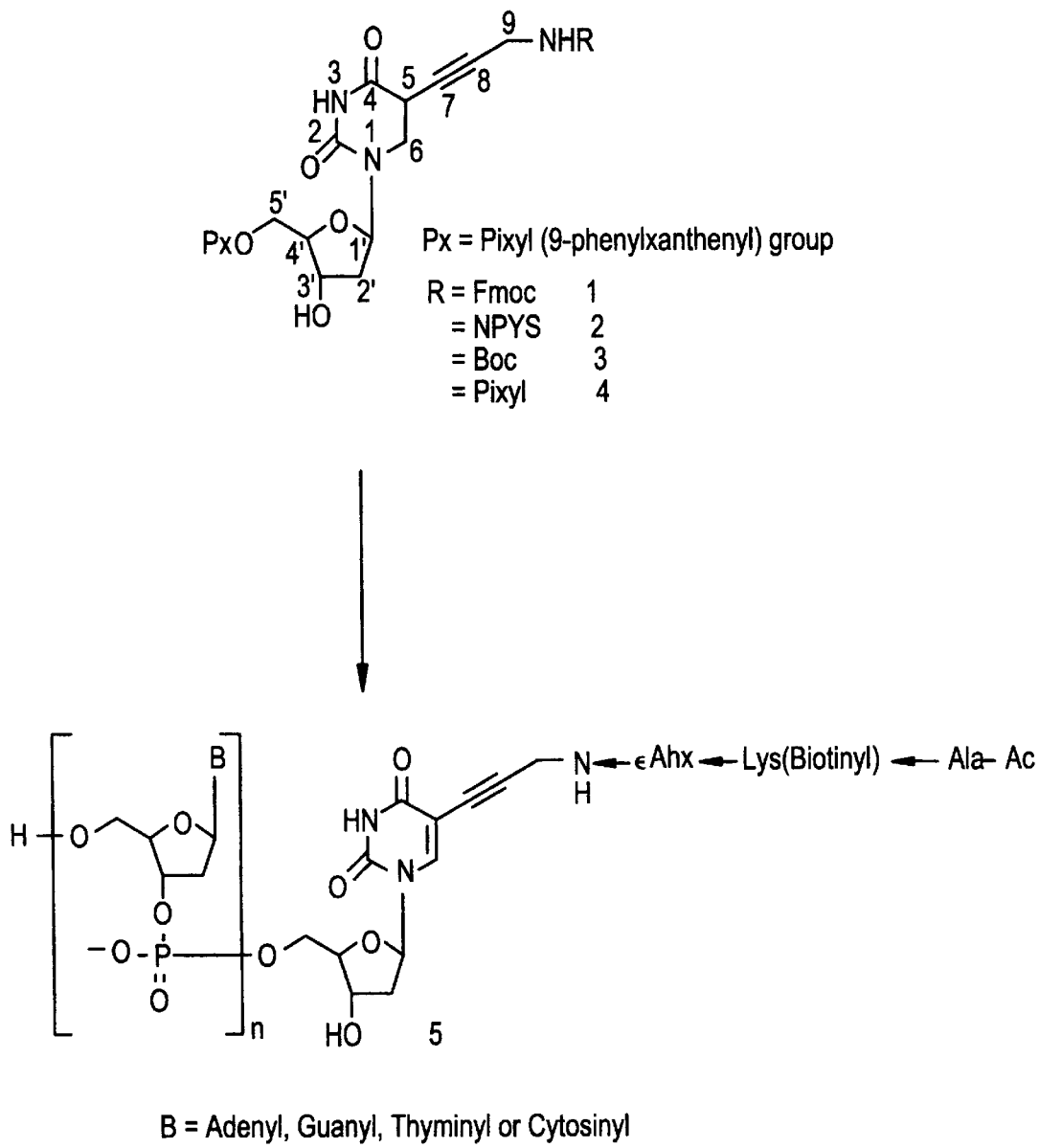
FIG. 2 shows an outline (SCHEME I) for producing compounds according to the present invention.
Figure 3:
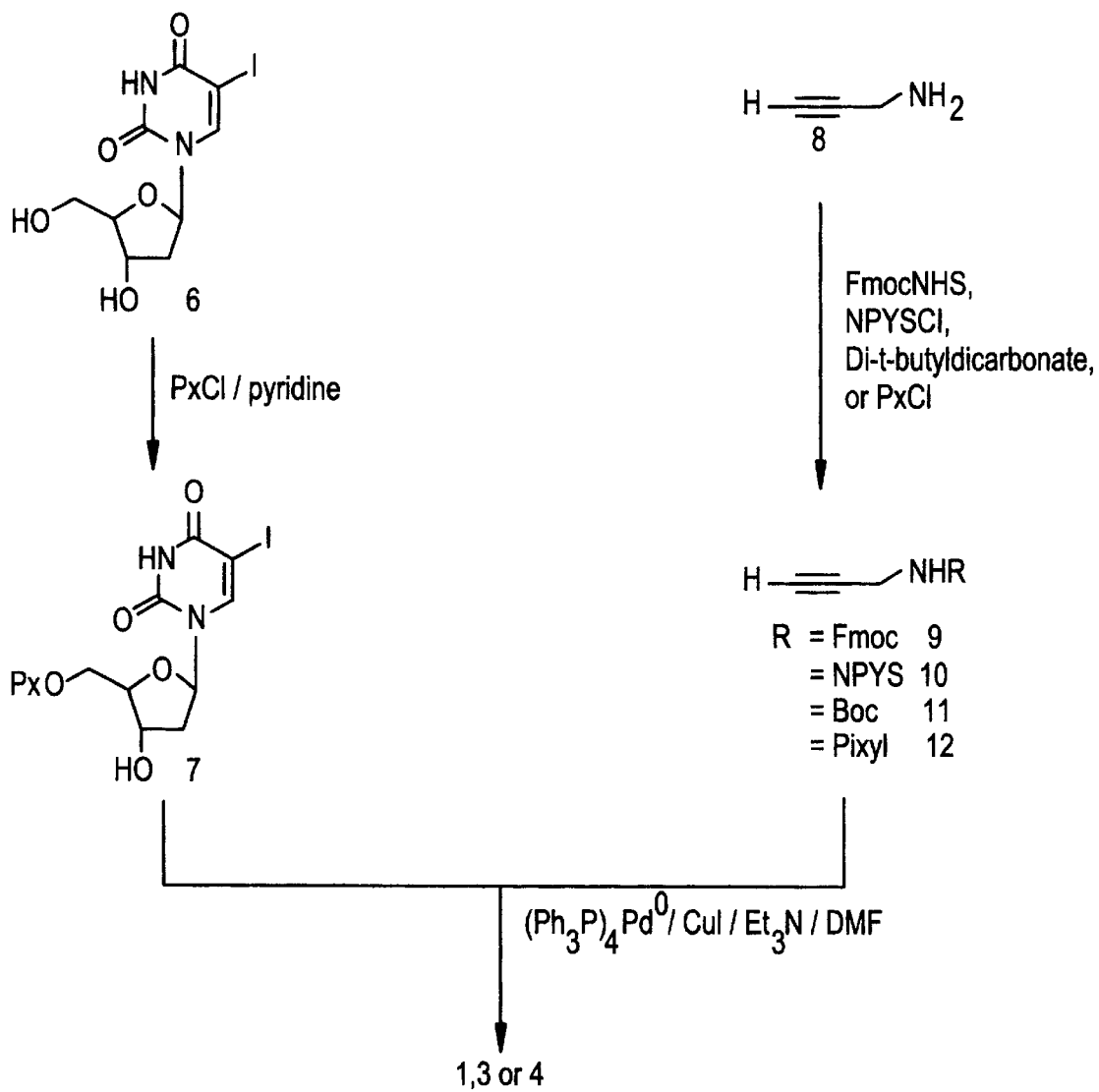
FIG. 3 shows detailed description (SCHEME II) for making the reactants in FIG. 2.
Figure 4:
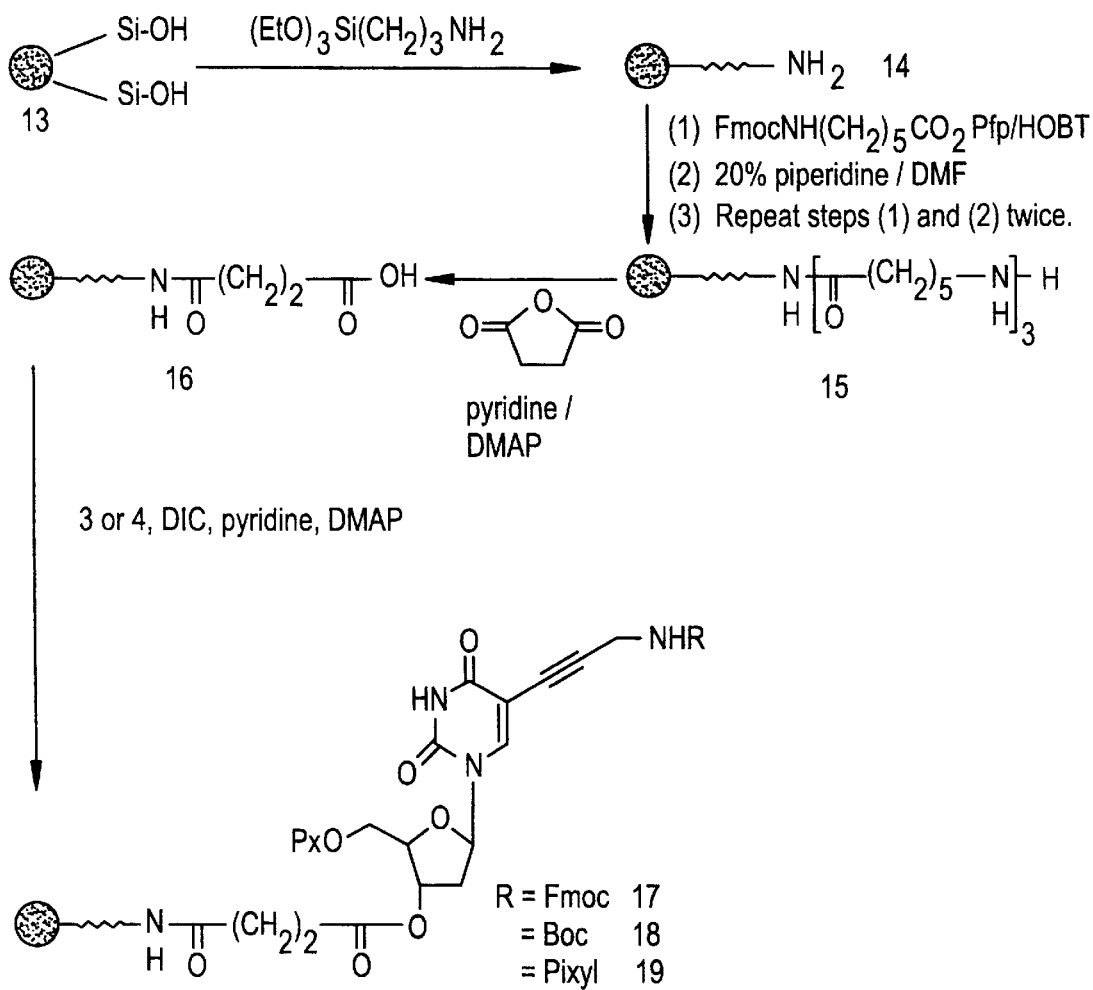
FIG. 4 shows the first part of detailed description (SCHEME III) for producing preferred compounds of the present invention.
Figure 5:
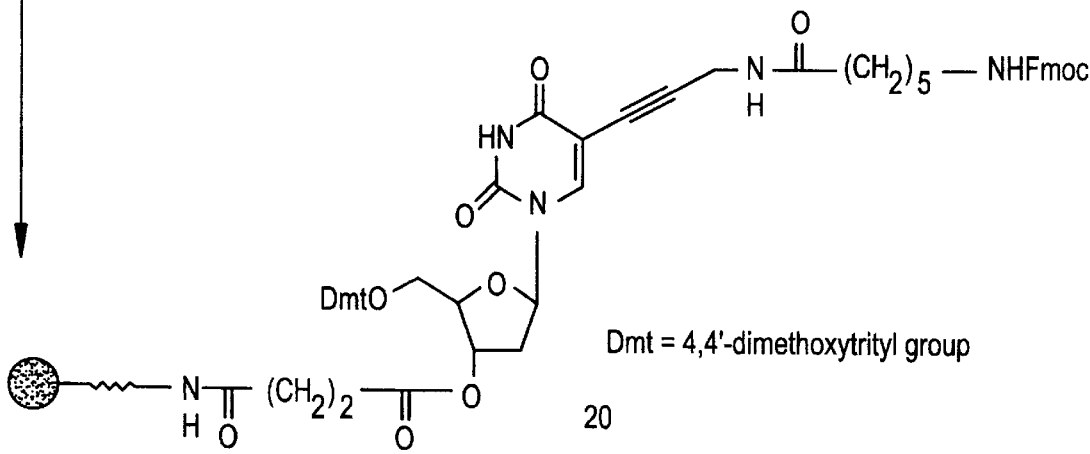
FIG. 5 shows the second part of the more detailed description in SCHEME III, which follows on from FIG. 4.
Figure 6:
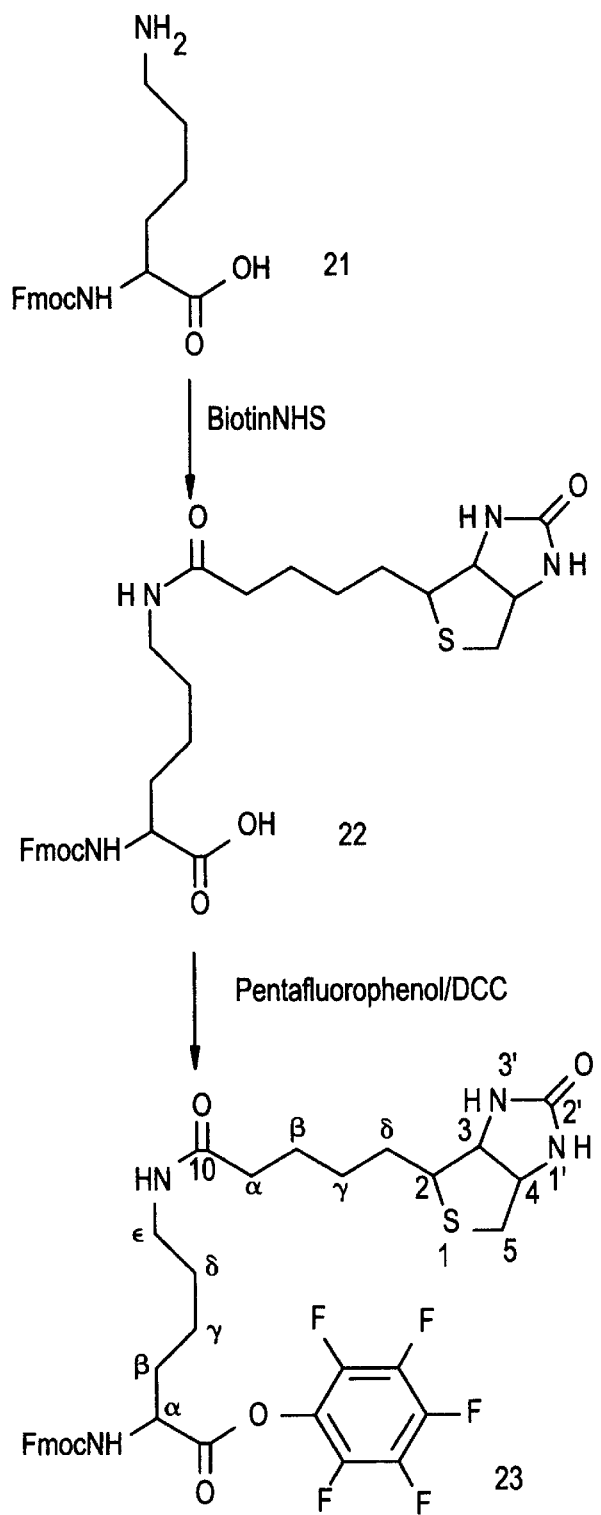
FIG. 6 shows more description for producing the labelled amino acids used in the peptide synthesis of the invention.

Specific embodiments of this invention will now be described, by way of the following non-limiting examples. The compounds prepared are frequently referred to by way of reference numbers which are shown in FIGS. 2 to 6 in the drawings.

EXAMPLE 1

MATERIALS: 3-Aminopropyne, 5-iodo-2'-deoxyuridine, biotin and 3-aminopropyl-triethoxysilane were purchased from Sigma. N-(Fluoren-9-ylmethoxy-carbonyloxy)-succinimide, $N^{\alpha}$-Fmoc-L-lysine, pentafluorophenol, DCC, and Fmoc-Ala-OPfp were obtained from Auspep, Melbourne. 3-Nitropyridine-2-sulfenyl chloride was obtained from Kokusan, Tokyo. 9-Chloro-9-phenylxanthene and tetrakis(triphenylphosphine)palladium(0) were supplied by Aldrich. N-hydroxysuccinimide was obtained from Pierce. Triethylamine (puriss grade), Controlled Pore Glass (200–400 mesh, 500 Å pore size, Cat. no. 27720) and diisopropylcarbodiimide (DIC) were purchases from Fluka. Reagents for the ninhydrin assay were supplied by Applied Biosystems. DMF was distilled under reduced pressure and used within 14 days. Pyridine was distilled over $CaH_2$ at atmospheric pressure, and stored over 5 Å molecular sieves. All other reagents were used without further purification. Thin layer chromatograph was performed on Merck SG-60 precoated plastic plates, and flash chromatography was performed on Merck silica gel (SG-60, 230–240 mesh). Biotin-N-hydroxysuccinimidyl ester was prepared as described previously[1] except that 95% ethanol/1% acetic acid/4% H2O was substituted as recrystallisation solvent. N-Fmoc-εAhx-OPfp[2] and N-Boc-3-aminopropyne[3] were prepared according to literature methods.

Melting points were taken on an Electrothermal apparatus and are uncorrected. NMR spectra were recorded on a JEOL GX400 spectometer operating at 399.9 MHz for $^1H$ observation and at 99.98 MHz for $^{13}C$ observation. DEPT experiments were performed with a 135° $^1H$ selection pulse. The DQF-COSY experiment was run in the phase-sensitive mode of data accumulation with a 356×2K data matrix and 16 transients per increment. The spectrum was obtained after zero-filling to a 1K×1K final data matrix and application of an exponential weighting function in both directions. The HMBC experiment was run in the absolute absorption mode with a 128×2K raw data matrix and 128 transients per increment. The spectrum was obtained after zero-filling 4 times in the t, dimension and application of a sine-bell weighting function in both directions. The experiment was run assuming a $^{32}C$-H value of 8Hz. The numbering system used for nucleosides 3 and 4 is outlined in Scheme I while the numbering system for compounds 22 and 23 is as shown in Scheme IV. IR spectra were recorded on a Perkin Elmer 1600 series FIR, using KBr discs. UV spectra were recorded with samples dissolved in 0.1 mM EDTA solutions, on a Varian Cary 1 spectrophotometer. Amino-acid analyses were performed on a Beckman System 6300 Amino Acid Analyser. HPLC analyses were performed on a Shimadzu LC4A instrument using a Phenomenex reverse-phase $C_{18}$ column (5 ODS 30, 5 µm, 60 Å pore size), with buffer A being 0.1M triethylammonium acetate, pH 7.0 and buffer B 0.1M triethylammonium acetate, 30% $CH_3CN$, pH 7.0.

Elemental analyses were obtained from CMAS Pty. Ltd., Melbourne. High and low resolution FAB mass spectra were recorded on JEOL DX-300 and JEOL AX-505H instruments respectively, equipped with FAB sources. Samples for high resolution measurements were suspended in a polyethylene glycol (600)/thiolglycerollglycerol/DMSO matrix; low-resolution samples in a thioglycerol matrix. The ionisation gas in both cases was Xe.

SYNTHESIS OF REAGENTS

EXAMPLE 1(a)

3-(fluoren-9-yl-methoxycarbonyl)-amidopropyne (9)

3-Aminopropyne (359 µL, 5.25 mmol) was added dropwise to a solution of N-(fluoren-9-ylmethoxycarbonyloxy)succinimide (FmocNHS) (1.69 g, 5.00 mmol) in THF (8 mL) at 0° C. and stirred for 2 h. The solution was allowed to warm up to room temperature and the solvent was removed under vacuum. The crude residue was dissolved in ethyl acetate (100 mL) and the solution washed with $H_2O$ (3×30 mL), then dried ($Na_2SO_4$). Recrystallisation from ethyl acetate gave 9 as colourless needles (1.11 g, 80%), mp 129–130° C. $^1H$ NMR ($d_6$-DMSO): δ3.13 (t, 1H, H1, J=2.3 Hz), 3.80 (dd, 2H, H3, J=5.9, 2.5 Hz), 4.23 (t, 1H, Fmoc CH, J=6.8 Hz), 4.33 (d, 2H, Fmoc $CH_2$, J=7.1 Hz), 7.33 (ddd, 2H, Fmoc H2 and H7, J=7.6, 7.5, 1.2 Hz), 7.41 (ddd, 2H, Fmoc H3 and H6, J=7.6, 7.5, 0.9 Hz), 7.71 (d, 2H, Fmoc H2 and H8, J=7.6 Hz), 7.81, (t, 1H, NH, J=5.9 Hz), 7.90 (d, 2H, Fmoc H4 and H5, J=7.6Hz). $^{13}C$ NMR ($d_6$-DMSO): δ29.8 (C3), 46.6 (Fmoc CH, 65.7 (Fmoc $CH_2$), 73.1 (C1), 81.4 (C2), 120.1 (Fmoc C3 and C6), 125.2 (Fmoc C2 and C7), 127.1 (Fmoc C4 and C5), 127.6 (Fmoc C1 and C8), 140.7 (C4a and C4b), 143.8 (Fmoc C8a and C9a), 155.9 (Fmoc CO). FABMS m/z 300 (M+Na), 278 (M+H). Anal. calcd for $C_{18}H_{15}NO_2$: C, 78.0; H. 5.45; N, 5.05. Found: C, 78.1; H, 5.45; N, 5.01.

EXAMPLE 1(b)

3-(3-Nitro-2-sulfenylpyridine)-aminopropyne (10)

To a stirred solution of $^3$-aminopropyne (855 µL, 12.5 mmol) in DMF (20 mL) was added 3-nitropyridine-2-sulfenyl chloride (0.94 g, 5.0 mmol) in two equal portions over 0.5 h. After 1.5 h, the reaction mixture was poured into ethyl acetate (500 mL) and washed with $H_2O$ (3×200 mL), dried ($Na_2SO_4$), and the solvent removed under vacuum. Recrystallisation from MeOH/$H_2O$ gave 10 as red crystals (0.653 g, 62%), mp 107–9° C. $^1H$ NMR ($d_6$-DMSO): δ3.18 (t, 1H, H1, J=2.6 Hz), 3.77 (dd, 2H, H3, J=4.4, 2.6 Hz), 5.34 (t, 1H, NH, J=4.4 Hz), 7.47 (dd, 1H, NPYS H5, J=8.3, 4.6 Hz), 8.61 (dd, 1H, NPYS H6, J=8.4, 1.5 Hz), 8.90 (dd, 1H, NPYS H4, J=4.4, 1.5 Hz). $^{13}C$ NMR ($d_6$-DMSO): δ30.7 (C3), 74.8 (C1), 81.7 (C2), 120.4 (NPYS C5), 134.3 (NPYS C4), 139.8 (NPYS C3), 154.1 (NPYS C6), 163.1 (NPYS C2). FABMS m/z 210 (M+H). Anal. calcd for $C_8H_7N_3O_2S$: C, 45.9; H, 3.37; N, 20.1. Found: C, 45.7; H, 3.33; N, 20.1.

EXAMPLE 1(c)

$^3$-(9-Phenylxanthen-9-yl)aminopropyne (12)

9-Chloro-9-phenylxanthen (14.7 g, 50 mmol) was added in two equal portions over 0.5 h to a stirred solution of 3-aminopropyne (8.6 mL, 125 mmol) in DMF (100 mL). After 3 h, MeOH (20 mL) was added and the reaction mixture was stirred for 15 min. The mixture was then extracted into diethyl ether (500 mL) and washed with $H_2O$ (3×300 mL), dried ($Na_2SO_4$), and the solvent removed under vacuum. The resulting yellow oil was dried under high vacuum (4 h), and then redissolved in hot diethyl ether (70 mL). The solution was kept at −20° C. for 24 h and then filtered, the solid washed with ice-cold hexand (2×50 mL) followed by ice-cold diethyl ether (2×50 mL), giving 12 as a colourless powder (12.7 g, 82%), mp 116–8° C. $^1H$ NMR ($d_6$-DMSO): δ2.86 (dd, 2H, H3, J=7.3, 4.4 Hz), 2.99 (t, 1H, H1, J=2.4 Hz), 4.01 (t, 1H, NH, J=7.2 Hz), 6.98–7.50 (m, 13H, Px CH). $^{13}C$ NMR ($d_6$-DMSO): δ32.8 (C3), 59.7 (Px C9), 73.4 (C1), 82.7 (C2), 1160.0 and 123.5 (Px CH), 125.0 (Px C8a and C9a), 126.3, 126.4, 128.0, 128.6, 128.7 (Px CH), 149.5 (Px C1'), 150.7 (Px C4a and C10a). FABMS m/z 311 (M+). Anal. calcd for $C_{22}H_{17}NO$: C, 84.8; H, 5.51; N,4.50. Found: C, 84.4; H. 5.73; N, 4.30.

EXAMPLE 1 (d)

5-Iodo-5'-O-(9-phenylxanthen-9-yl)-2'-deoxyuridine (7)

5-Iodo-2'-deoxyuridine (IDU) (3.54 g, 10 mmol) was coevaporated with dry pyridine (3×20 mL). The IDU was redissolved in dry pyridine (15mL) and 9-phenyl-9-chloroxanthen (3.82 g, 13 mmol) was added to the stirring solution in two equal portions over 0.5 h. After 1h, MeOH (5 mL) was added and the solution stirred for a further 0.5 h. The solvent was then removed under vacuum, and the residue recrystallized from a 1% $Et_2N$/ethyl acetate solution giving 7 as colourless crystals (4.27 g, 70%), mp 200–2° C. $^1H$ NMR ($d_6$-DMSO): δ2.20 (m, 2H, H2'), 2.99 (dd, 1H, H5', J-10.5, 4.2 Hz), 3.10 (dd, 1H, H5", J=10.5, 2.7 Hz), 3.85 (m, 1H, H4'), 4.15 (m, 1H, H3'), 5.29 (d, 1H, 3'OH, J=4.2 Hz), 6.08 (t, 1H, H1', J=7.0 Hz), 7.10–7.42 (m, 13H, Px CH), 8.08 (s, 1H, H6). $^{13}C$ NMR ($d_6$-DMSO): δ40.4 (C2'), 63.8 (C5'), 69.9 (C5), 71.0 (C3'), 75.6 (Px C9), 85.2 (C1'), 85.9 (C4'), 116.3, 116.4 (Px CH), 122.3, 122.4 (Px C8a and C9a), 123.8, 124.0, 125.8, 126.8, 128.2, 129.3, 129.69, 129.7, 129.73 (Px CH), 143.9 (C6), 148.4(Px C1'), 150.0 (C2), 150.51, 150.58 (Px C4a and C10a), 160.6 (C4). FABMS m/z 633 (M+Na'). Anal. calcd for $C_{28}H_{23}N_2P_6I$: C, 55.1; H,3.81, N, 4.59. Found: C, 55.0; H, 3.81, N, 4.54.

EXAMPLE 1(e)

5-[3(-tert-Butyloxycarbonylamido)prop-1-yn-1-yl)]-5'-O-(9-phenyl-xanthen-9-yl)-2'-deoxyuridine (3)

To a degassed (Ar) solution of 11 (1.22 g, 2.00 mmol) in DMF (6mL) was added CuI (0.076 g, 0.40 mmol), $Et_3N$ (558 μL, 4.00 mmol), 3-tery-butyloxycarbonylamidopropyne[11] (0.932 g, 6.00 mmol) and $(Ph_3P)_4Pd^o$ (0.232 g, 0.20 mmol) successively and the solution was stirred for 5 h. AB1X8 ($HCO_3$—) ion-exchange resin (6 molar equiv) was added with MeOH (10 mL) and $CH_2Cl_2$ (10 mL), and the mixture stirred for 30 min. The resin was removed by filtration, and the solvent removed under reduced pressure. The crude residue was dissolved in ethyl acetate (200 mL), the solution was washed with $H_2O$ (3×100 mL), dried ($Na_2SO_4$), and filtered. After removal of the solvent, flash silica gel chromatography (70 g silica, 0–10% MeOH/$CH_2Cl_2$) followed by recrystallisation from chloroform/diethyl ether gave 3 (0.602 g, 47%) as colourless crystals, mp 157–160° C. $^1H$ NMR ($d_6$DMSO): δ1.35 (s, 9H, Boc $CH_3$, 2.25 (m, 2H, H2'), 3.00 (dd, 1H, H5', J=10.5, 4.4 Hz), 3.12 (dd, 1H, H5", J=10.4, 2.6 Hz), 3.69 (m, 2H, H9), 3.91 (m, 1H, H4'), 4.15 (m, 1H, H3'), 5.30 (d, 1H, 3'OH, J=4.2 Hz), 6.09 (5, 1H, H1', J=6.7 Hz), 7.10–7.45 (m, 13H, Px CH), 7.96 (s, 1H, H6). $^{13}C$ NMR (d6-DMSO): δ28.2 (Boc $CH_3$), 30.0 (C9), 40.3 (C2'), 63.8 (C5'), 70.8 (C3'), 73.8 (C8), 75.5 (Px C9), 78.2 (Boc C), 85.3 (C1'), 85.9 (C4'), 90.1 (C7, 98.4 (C5), 116.1, 116.3 (Px CH), 122.0 (Px C8a and C9a), 123.9, 124.0, 125.8, 126.7, 128.1, 129.0, 129.1, 129.7 (Px CH), 142.9 (C6), 148.3 (Px C2), 149.3 (C1'), 150.5, 150.7 (Px C4a and C10a), 155.1 (Boc CO), 161.6 (C4). FABMS m/z 660 (M+Na). Anal. calcd for $C_{36}H_{35}H_3O_8$ C, 67.8; H, 5.54; N, 6.59. Found C, 67.7; H, 5.68; N, 6.54.

EXAMPLE 1(f)

The Fmoc-nucleoside 1 was prepared in an analogous manner but it could not be purified ( to analytical purity due to persistent contaminating starting nucleoside 7. $^{13}C$ NMR ($CDCl_3$): δ31.2 (C9), 41.8 (C2'), 46.9 (Fmoc C9), 60.3 (C5'), 63.4 (C8), 66.4 (Fmoc CH2), 72.4 (C3'), 74.3 (Px C9), 86.1 (C1'), 86.7 (C4'), 89.5 (C7), 99.4 (C5), 116.4 (Px CH), 119.8 (Fmoc C3 and C6), 122.1, 122.3 (Px C8a and C9a), 123.7, 123.8 (Px CH), 124.8 (Fmoc C2 and C7), 126.2 IPx CH), 126.85, 126.95 (Fmoc C4 and C5), 127.8 (Fmoc C1 and C8), 129.4, 129.6 (Px CH), 141.1 (Fmoc C4a and C4b), 143.2, 143.6 (Fmoc C8a and C9a), 143.7 (C6), 148.1 (C2), 149.4 (Px C1'), 151.06, 151.12 (Px C4a and C10a), 155.6 (Fmoc CO), 162.25 (C4).

EXAMPLE 1(g)

5-[3-(Phenylxanthen-9-ylamino)prop-1-yn-1-yl]-5'-O-(9-phenyl-xanthen-9-yl)-2'-deoxyuridine (4)

The procedure was identical to that of 3 except that the crude residue was redissolved in $CH_2Cl_2$ (200 mL). The solution was washed with 10% $NaHCO_3$ (2×100 mL) and $H_2O$ (1×100 mL). After the solution had been dried ($Na_2SO_4$), filtered, and the solvent evaporated, flash silica gel chromatography (0–5% MeOH/$CH_2Cl_2$. 1% $Et_3N$) gave 4 as a fawn solid (0.608 g, 76%). The portion was recrystallised from MeOH to analytical purity, mp 156–8° C. (decomp.). $^3H$ NMR ($d_6$-DMSO): δ2.25 (m, 2H, H2'), 2.55 (dd, 1h, H9a, J=16.3, 7.15 Hz), 2.66 (dd, 1H, H9b, J=16.3, 7.14 Hz), 2.95 (dd, 1H, H5', J=10.6, 3.67 Hz), 3.07 (dd, 1H, H5", J=10.4, 2.38 Hz), 3.51 (t, 1H, N9H, J=7.20Hz), 3.9 (m, 1H, H4'), 4.21 (m, 1H, H3'), 5.31 (d, 1H, 3'OH, J=4.03 Hz), 6.11 (t, 1H, H1', J=6.78 Hz), 6.85–7.40 (m, 26H, NPx and OPx CH), 8.05 (s, 1H, H6), 11.6 (br s, 1H, H3). $^{13}C$ NMR ($d_6$-DMSO): δ33.4 (C9), 40.8 (C2'), 59.6 (NPx C9), 63.6 (C5'), 70.9 (C3'), 74.6 (C8, 75.7 (OPX C9), 85.2 (C1'), 86.0 (C4'), 91.2 (C7), 115.86, 115.91, 116.21, 116.30 (NPx and OPx CH), 122.17 and 122.24 (OPx C8a and C9a), 123.50, 123.54, 123.92, 124.05 (NPx and OPx CH), 124.65, 124.68 (NPx C8a and C9a), 125.7, 126.3, 126.5, 127.8, 127.9, 128.46, 128.58, 128.68, 128.74, 128.98, 129.25, 129.64, 129.76 (NPx and OPx CH), 142.7 (C6), 148.1 (C2), 149.3 (NPx and OPx C1'), 150.4, 150.61, 150.66, 150.75 (NPx and OPx C4a and C10a), 161.6 (C4). FABMS m/z 816 (M+Na), 794 (M+H). HR-FABMS exact mass found 794.2871, calculated for ($C_{50}H_{39}N_3O_7$)+H 794.2868.

EXAMPLE 1(h)

$N^\alpha$-(FIuoren-9-ylmethoxycarbonyl)-Nε-biotinyllysine, Fmoc-Lys(Biotin)-OH (22)

A solution of $Et_3N$ (698μL, 5.00 mmol) in DMF (70 mL) was added to a mixture of the N-hydroxysuccinimidyl ester of biotin (3.41 g, 10.0 mmol) and $N^\alpha$-Fmoc-lysine 21 (1.84 g, 5.00 mmol), and the resulting mixture was stirred for 6 h, then filtered. Cold aqueous HCl (pH 2, 500 mL) was then added and the precipitate was filtered and washed with aqueous HCl (pH2, 3×200 mL) and H$_2$O (3×200 mL). The residue was found to contain a large amount of water at this stage and was consequently lyophilised (48 h) to give a fluffy colourless solid (2.41 g, 81%), mp 181–2° C. (decomp.). $^1$H NMR (d$_6$-DMSO): δ1.20–1.40 (m, 4H, Btn Hγ and Lys Hδ), 1.50–1.52 (m, 6H Btn Hβ and Btn Hδ and Lys Hγ), 1.52–1.62 (m, 2H, Lys Hβ), 2.03 (t, 2H, Btn Hα, J=7.3 Hz), 2.56 (d, 1H, Btn H5b, J=12.5 Hz), 2.79 (dd, 1H, Btn H5a, J=12.4, 5.1Hz), 3.00 (m, 2H, Lys H11), 3.06 (m, 1H, Btn H2), 3.9 (m, 1H, Lys Hα), 4.1 (m, 1H, Btn H3), 4.18–4.30 (m, 4H, Btn H4 and Fmoc CH$_2$and Fmoc H9), 6.36 (s, 1H Btn H1'), 6.42 (s, 1H, Btn H3'), 7.32 (ddd, 2H, Fmoc H2 and H7, J=7.4, 7.4, 1.1 Hz), 7.41 (dd, 2H, Fmoc H3 and H6, J=7.2, 7.2 Hz), 7.61 (d, 1H, Lys N$^\alpha$H, J=8.1 Hz), 7.72 (d, 2H, Fmoc H1 and H8, J=7.4 Hz), 7.76 (t, 1H, Lys N$^\alpha$H, J=5.6 Hz), 7.88 (d, 2H, Fmoc H4 and H5, J=7.4 Hz). $^{13}$C NMR (d$_6$-DMSO): d 23.1 (Lys Cγ), 25.3 (Btn Cβ), 28.0 (Btn Cδ), 28.2 (Btn Cγ), 28.8 (Lys Cδ), 30.5 (Lys Cβ), 35.2 (Btn Cα), 38.2 (Lys Cε), 39.9 IBtn C5), 46.7 (Fmoc C9), 53.8 (Lys Cα), 55.2 (Btn C2), 59.2 (Btn C4), 61.0 (Btn C3), 65.6 (Fmoc CH$_2$), 120.1 (Fmoc C3 and C6), 125.3 (Fmoc C2 and Cy), 127.1 (Fmoc C4 and C5), 127.7 (Fmoc C1 and C8), 140.7 (Fmoc C4a and C4b), 143.79, 143.84 (Fmoc C8a and C9a), 156.2 (Fmoc CO), 162.7 (Btn C2'), 171.9 (Btn C10), 174.0 (Lys CO$_2$H). HR-FABMS exact mass found 595.2566, calculated for (C$_{31}$H$_{38}$N$_4$O$_6$S)+H 595.2590. IR 1702 cm$^{-1}$ (Fmoc CO and Lysine α CO), 1638 cm$^{-1}$ (amide CO).

EXAMPLE 1(i)

N$^\alpha$-(Fluoren-9-ylmethoxycarbonyl)-N$^\epsilon$-biotinyllysine pentafluoro-phenyl ester, Fmoc-Lys(Biotin)-OPfp (23)

A solution of pentafluorophenol (1.75 g, 9.29 mmol) and DCC (1.27, 6.32 mmol) in DMF (5 mL) was added to the solution of 22 (2.21 g, 3.72 mmol) in DMF (40 mL) and the mixture stirred for 16 h. The colourless precipitate was filtered off and discarded. The filtrate was kept and after removal of the solvent under vacuum followed by trituration and diethyl ether (4×10 mL) to afford a colourless solid which was recrystallised from ethyl acetate/ethanol/acetic acid (80:19:1) to give fine colourless crystals (1.90 g, 67%), mp 162–5° (decomp.). $^1$H NMR (d$_6$DMSO): δ1.23–1.32 (m, 2H, Tbh Hγ), 1.38–1.53 (m, 6H, Btn Hβ and Btn Hδ and Lys Hδ), 154–163 (m, 2H, Lys Hβ), 2.04 (t, 2H, Btn Hα: J=7.3 Hz), 2.55 (d, 1H, Btn H5b, J=12.5 Hz), 2.79 (dd, 1H, Btn H5a, J=12.5, 5.1 Hz), 2.98–3.04 (m, 2H, Lys Hε), 3.05–3.10 (m, 1H, Btn H2), 4.09 (m 1H, Lys αH), 4.20–4.30 (m, 2H. Btn H3 and Fmoc H9), 4.32–4.42 (m, 3H, Btn H4 and Fmoc CH$_2$), 6.35 (s, 1H, Btn H1'), 6.42 (s, 1H, Btn H3') 7.28–7.34 (m, 2H, Fmoc H2 and H7, 7.40 (dd, 2H, Fmoc H3 and H6, J=7.5, 7.5 Hz), 7.70 (d, 2H, Fmoc H1 and H8, J=7.3 Hz), 7.77 (5, 1H, Lys NeH, J=5.7 Hz), 7.88 (d, 2H, Fmoc H4 and H5, J=7.7 Hz), 8.12 (d, 1H Lys N$^\alpha$H, J=7.3 Hz). $^{13}$C NMR (d$_6$-DMSO): δ22.7 (Lys Cγ), 25.3 (Btn Cβ), 28.1 (Btn Cδ), 28.3 (Btn Cγ). 28.7 (Lys Cδ), 29.9 (Lys Cβ), 35.3 (Btn Cα), 38.1 (Lys Cε), 39.9 (Btn C5), 46.7 (Fmoc C9), 53.9 (Lys Cα), 55.5 (Btn C2), 59.2 (Btn C4), 61.1 (Btn C3), 65.9 (Fmoc CH$_2$), 120.2 (Fmoc C3 and C6), 125.2 (Fmoc C2 and C7), 127.1 (Fmoc C4 and C5), 127.7 (Fmoc C1 and C8), 136.5, 138.5, 139.0 (2 x m, C-CF), 140.8 (Fmoc C4a and C4b), 142.0 (m, C-CF), 143.68, 143.71 (Fmoc C8a and C9a), 156.2 (Fmoc CO), 162.7 (Btn C2'), 169.2 (Lys CO), 171.9 (Btn ClO). HR-FABMS exact mass found 761.2413, calculated for (C$_{37}$H$_{37}$N$_4$O$_6$SF$_5$)+H 761.2432. IR 1787 cm$^{-1}$ (ester CO), 1702 cm$^{-1}$ (Fmoc CO), 1641 cm$^{-1}$ (amide CO).

EXAMPLE 1(j)

Preparation of Succinyl-CPG resin (16)

A solution of 3-aminopropyltriethoxysilane (3 g, 13.6 mmol) in ethanol (60 mL) was added to CPG (200–400 mesh, 500 Å pore size, Cat. No. 27720) 13 (6 g), and the mixture was shaken gently at regular intervals over a period of 6 h. The resin was collected by gravity filtration (without any washing), air dried (24 h), and kept at 110° C. (24H) to give the aminated resin 14. The amino loading was determined to be 129 μmol/g by ninhydrin assay. N-Fmoc-εAhx-OPfp (2.5 molar equiv) and HOBT (2.5 molar equiv) in DMF were coupled to 14 (double coupling, 1.5 h each reaction) in a sintered-glass column. Two or more amino-hexanoic acid residues were attached using 1.5 h single couplings, giving resin 15. The Fmoc group was cleaved by treatment with 20% piperidine/DMF (5 min), the resin washed with DMF, and then a solution of succinic anhydride (50 molar equiv) and DMP (10 molar equiv.) in a minimum volume of dry pyridine was added. After shaking the suspension for 1 h, the resin was rinsed with pyridine, DMF, CH$_2$Cl$_2$, and dried under vacuum. The reaction was monitored by ninhydrin assay, and the loading of carboxylic acid groups as calculated from the disappearance of amino groups was 46 μmol/g.

EXAMPLE 1(k)

Coupling of Modified Nucleosides 3 and 4 to Succinyl-CPG Resin 16:

Resin 16 was treated twice with a solution of 3 or 4 (5 molar equiv), diisopropylcarbodiimide (5 molar equiv) and DMAP (0.5 molar equiv) in a minimum volume of dry pyridine in two separate 16 h couplings with only a washing set up in between (double coupling). After the second coupling, the resin was rinsed with pyridine, and pixyl assay gave a nucleoside loading of 39 μmol/g. The remaining carboxylic acid and amino groups were capped with piperidine and Ac$_2$O/DMAP according to the method of Damha[4], giving resins 18 or 19.

EXAMPLE 1(l)

Derivatisation of 18 and 19 to give 20

In the case of 18, the resin was treated with 90% TFA/ethanedithiol for 10 min, rinsed with CH$_2$Cl$_2$, and then neutralised with 20%/a Et$_3$N/CH$_2$Cl$_2$. The resin was then rinsed with CH$_2$Cl$_2$ dried, and treated with a 1:1 mixture of Fmoc-εAhx-OPfp/HOBT in DMF (2.5 molar equiv, 45 min, twice). After rinsing with DMF, the resin was subjected to two successive 16 h reactions with 4,4'-dimethoxytrityl chloride (k50 molar equiv each time) in a minimum volume of dry pyridine to give resin 20. Trityl assay showed 30 μmol/g of dimethoxytrityl group present. The procedure for the derivatisation of 19 to give 20 is identical to the procedure for 18 except that 3% DCA/CH$_2$Cl$_2$was substituted for 90% TFA/ethanedithiol.

EXAMPLE 1(m)

Polyamide and Oligonucleotide Synthesis on Resin 20

A biotinylated lysine residue and an alanine residue were attached to 20 by Fmoc solid phase peptide synthesis, using 23 and N-Fmoc-Ala-OPfp respectively, in a manual glass-sinter peptide synthesis cell. A 5-fold excess of amino-acid pentafluorophenyl ester and HOBT was used, with a coupling time of one hour and 20% piperidine/DMF as deprotection agent. The α-amino group of alanine was deprotected and capped with Ac$_2$O (25 μL) and DMAP (0.050 g)

in dry pyridine (0.5 h). After rinsing with DMF, $CH_2Cl_2$ and drying under vacuum, a portion of the resin was used in oligonucleotide synthesis on an Applied Biosystems 380 A DNA Synthesizer' using standard β-cyanoethyl-protected phosphoramidites (with a 60 sec Ac2O/DMAP capping step[2]), on a 1 μmol scale. The sequence of the oligonucleotide synthesised was GATGAGTTCGTGTCCGTA-CAACT* (T* being the modified nucleoside linker). The resulting conjugate was cleaved from the solid support by treatment with concentrated ammonia (22° C., 6h). The resulting solution of the conjugate was heated at 50° C. for 24 h to effect base deprotection. The ammonia was removed under reduced pressure and the conjugate redissolved in 0.1 mM EDTA (2 mL). Separation by preparative PAGE (16% polyacrylamide gel)[5] showed two products, the one of the lowest electrophoretic mobility was purified to give 5 in an overall yield of 2.1%.

EXAMPLE 1(n)

Characterisation of the Oligonucleotide-Polyamide Conjugate:

A sample of the conjugate 5 was 5'-end labelled[5] with γ-[$^{32}$P]-ATP and $T_4$ polynucleotide kinase and was shown to be homogeneous by PAGE (16% polyacrylamide gel). The UV spectrum showed a maximum of absorption at 260 nm. A 3.0 nmol aliquot of the conjugate (amount calculated from UV absorption at 260nm) was analysed for amino-acid content, and showed a ratio of 1.01 mol Ala to 0.99 mol Lys as expected, the amount of peptide found in the sample was 2.55 nmol. A 1 μg aliquot of 5 (in 20 μL of H2O) was incubated with P, nuclease (5 μg, in 5 μL of 0.05M NaOAc, pH 6.0) and 0.5M NaOAc (pH 6.0, 2 μL) at 37° C. for 30 min. The resulting enymatic digest was analysed by reverse-phase $C_{18}$ HPLC, using a linear gradient of 0–100% B over 60 min. The HPLC profile was manually integrated to give nucleotide ratios: pdA (4.67), pdG (5.21), pdC (4.80), pdT (6.05), dG (1.27). Expected ratios: pdA (5.00), pdG (5.00), pdC (5.00), pdT (6.00), dG (1.00).

EXAMPLE 1(o)

Ninhydrin Assay:

This is a modified version of the original assay[6] which specified an incubation time of 7 min at 100° C. Accurately weighed aliquots of resin were treated with 76% w/w phenol/ethanol (4 drops from a Pasteur pipette), 0.0002M potassium cyanide/pyridine (8 drops), and 0.28M ninhydrin/ethanol (4 drops) at I 10° C. for 10 min. After dilution with 60% ethanol (3.8 mL), the absorptions were measured at 570 nm ($\epsilon$=15000M-$^{-1}$ cm$^{-1}$).

EXAMPLE 1(p)

Pixyl and Trityl Assays

Accurately weighed aliquots of resins were treated with 10% toluenesulfonic acid/acetonitrile (3 mL) for 10 min at room temperature. Absorptions were measured at 445 nm ($\epsilon$=4400 M$^{-1}$cm$^{-1}$) for pixyl and 507 nm ($\epsilon$=66500 M$^{-1}$cm$^{-1}$) for trityl.

EXAMPLE 1(q)

Fmoc Assay:[7]

Accurately weighed aliquots of resin were treated with piperidine (200 μL) and $CH_2Cl_2$ (200 μL) for 30 min at room temperature. After dilution with $CH_2Cl_2$ (3.6 mL), the absorptions were measured at 301 nm ($\epsilon$=7800 M$^{-1}$cm$^{-1}$).

EXAMPLE 2

RESULTS AND DISCUSSION

Synthesis of the Modified Nucleoside

The modified nucleosides 1, 3 and 4 which act as the linker between the oligonucleotide and the polyamide were synthesised in three steps starting from commercially-available 5-iodo-2'-deoxyuridine (IDU) 6 (Scheme II). The first step involved the preparation of the four different N-protected propargylamines 9 to 12 by reaction of 3-aminopropyne and N-(fluoren-9-ylmethoxycarbonyloxy) succinimide, 3-nitropyridine-2-sulfenyl chloride (NPYSCI), di-t-butyldicarbonate and 9-chloro-9-phenylxanthene respectively. In the case of the NPYS derivative 10, the presence of a base was necessary for efficient reaction. Triethylamine was found to readily effect nucleophilic substitution of the NPYSCI to form the quaternary ammonium salt [(Et$_3$N)S(C$_5$H$_3$NO$_2$)]+Cl$^-$, so a 2.5 molar excess of 3-aminopropyne was used to act as base as well. All four protected propargylamines were synthesised in high yield.

The synthesis of the desired alkynyl nucleosides was attempted by two routes: attachment of a protected propargylamine to C5 of the IDU followed by protection of the 5'-hydroxyl, and vice-versa. The Pd(O)-catalysed oxidative coupling of a protected aminoalkyne to the unprotected nucleoside resulted in complex mixtures inseparable by silica gel chromatography. Protection of the 5'-hydroxyl of IDU via DMP-catalysed alkylation with 9-chloro-9-phenylxanthene gave the 5'-protected nucleoside 7 in high yield and purity, and this was coupled with protected propargylamines 9 to 12, according to the method of Hobbs[8]. The reaction of the protected nucleoside 7 with the Fmoc-protected propargylamine 9 produced the desired product 1 in quite low yields (30%), probably due to partial deprotection of 9 by triethylamine. The free primary amino groups generated by the deprotection may also coordinate with the palladium catalyst and hinder the coupling reaction[8]. The product 1 coeluted with the starting material in silica gel chromatography under a wide range of eluting conditions, and both the $^1$H and $^{13}$C NMR spectra showed that it contained a small amount of 7. The coupling reaction between 7 and the NPYS-protected propargylamine 10 produced a complex mixture which could only be resolved by silica gel chromatography followed by $C_{18}$reverse-phase HPLC. Analysis of the HPLC fractions by $^1$H and $^{13}$C NMR spectroscopy and FABMS showed that none contained the desired product. In contrast, the coupling of the Boc and pixyl-protected propargylamines 11 and 12 to 7 were straightforward. The Boc-protected nucleoside 3 also coelutes with the starting nucleoside 7 but the product 3 could be isolated in high yield nevertheless due to the absence of significant contaminating amounts of 7. The preparation of the dipicylated nucleoside 4 could be monitored by TLC (5% MeOH/1% Et$_3$N/CH$_2$Cl$_2$ and the reaction was judged to be complete after 5 hours. This reaction also had a high yield.

Although the alkynyl nucleosides 3 and 4 have quite complex structures, adequate characterisation could be achieved by 1-dimensional $^1$H and $^{13}$C NMR spectroscopy, since the multiplets in the former compound are well separated and most of the latter's resonances correspond quite closely to those of analogous compounds we have previously reported[3]. Some salient features of the $^{13}$C NMR spectrum of these alkynyl nucleosides are the two resonances in the regions δ73.8–74.6 and δ90.1–91.2 corresponding to the alkynyl quaternary carbons C8 and C7 respectively (see Scheme I for numbering system). The downfield shift of C5 from δ69.9 in IDU to δ98.4–98.7 is consistent with the substitution of a quaternary alkynyl carbon for the iodine atom. All other resonances were consistent with the proposed structures of 3 and 4.

The next stage in the synthesis of the conjugate was the derivatisation of a solid support for polyamide and oligonucleotide synthesis. Controlled-pore glass (CPG) resin allows both the polyamide and the oligonucleotide to be synthesised efficiently. Conventional peptide synthesis resins such as Pepsyn K9 have a higher loading than CPG but efficient DNA synthesis by the phosphoramidite approach is not possible, so CPG is the solid support of choice.

Derivatisation of CPG resin for DNA synthesis is conventionally effected by amination of the CPG, followed by coupling with a nucleoside succinate active ester[10] or a carbodiimide coupling, typically with DCC[10,11]. Damha et al., (Nucleic Acids Research (1990), 18, pp. 3813–3821) has recently described a method for the attachment of nucleosides to succinylated CPG resin via a 1-(3'-dimethylaninopropyl)-3-ethylcarbodiimide (DEC)-mediated condensation. This procedure is more convenient since it obviates additional solution-phase manipulation of the nucleoside derivatives. The effectiveness of DEC compared to that of DCC has been attributed to its smaller steric requirement[11]. With this in mind, we anticipated that diisopropylcarbodiimide (DIC) might also be better than DCC. Hence, a comparison of DIC with DCC and DEC was undertaken using a standard nucleoside, 5'-O-dimethoxytrityl-N'-benzoyl-2'-deoxycytidine (dimethoxytrityl=di(p-methoxyphenyl)phenylmethyl). Succinylated-CPG resin was treated with the nucleoside, DMAP (0.5 molar equiv), and the appropriate condensation agent in dry pyridine. After 24 h, the degree of nucleoside coupling was assessed by trityl assay. The nucleoside loadings were determined to be 22, 18 and 30 μmol/g for DCC, DEC and DIC respectively, C indicating that DIC is the condensation reagent of choice.

The solid support for the synthesis of the conjugate was prepared in 4 steps starting from CPG resin 13 (Scheme III). The CPG was aminated with 3-aminopropyltriethoxysilane[12], and then three 6-aminohexanoic acid spacer residues were attached using standard Fmoc solid-phase peptide synthesis techniques[9] to give resin 15. It was anticipated that incorporation of the three spacer units would allow more efficient oligonucleotide synthesis due to the increased accessibility of the terminal resin-bound nucleoside to reagents, in an analogous manner to long-chain alkylamine (LCAA) CPG13. The aminated resin 15 was subjected to DMAP-catalysed succinylation with succinic anhydride to give resin 16. Attachment of the appropriate nucleoside to the succinyl resin 16 was achieved by DIC/DMAP-mediated condensation, and any free carboxylic acid and amine groups remaining were blocked[4] by DCC/4-nitrophenol/piperidine and acetic anhydride/DMAP treatments respectively.

The attachment of the Fmoc-nucleoside derivative 1 to the succinyl resin 16 was problematic. The use of DMAP is necessary to achieve adequate nucleoside loadings of approximately 30 μmol/g, but we have found[14] that the concentration used effects 45% cleavage of the Fmoc group in 24 hours. After two successive 24 h coupling reactions between the Fmoc-nucleoside I and the succinyl resin 16, comparison of the Fmoc and pixyl assays suggested that about half of the nucleoside had undergone amine deprotection, and was probably attached to the resin by an amide bond. This side product was not expected to interfere in the preparation of the desired conjugate since it would be expected to be stable to the final cleavage conditions and thus stay on the solid support. However, resin derivatized with the Fmoc-nucleoside 1 consistently gave very low yields of conjugate and was not further investigated.

The Boc and pixyl nucleosides 3 and 4 were readily coupled to the solid support 16 under the above conditions, resulting in loadings of 22 μmol/g and 40 μmol/g respectively as assessed by pixyl assay. Both the Boc and the pixyl derivatives 3 and 4 gave sufficient nucleoside loadings for efficient oligonucleotide synthesis, but the latter is preferred due to its facile preparation and the milder deprotection conditions required.

EXAMPLE 3

Preparation of the Biotinylated Lysine Synthon 23

Previously, we have incorporated biotin residues into conjugates via global biotinylation of the polyamide moiety after deprotection of the e-amino group of the lysine residues[15]. This batchwise approach gave limited control of the placement of the biotins and, in larger polyamides containing up to 10 lysine residues, where the biotinylation reaction does not go to completion, an uneven distribution of biotins may result. The synthon 23 (Scheme IV) allows the incorporation of biotins in a highly controlled manner using conventional Fmoc peptide synthesis. It was prepared in a two-step procedure by biotinylation of $N^\alpha$-Fmoc-L-Lys-OH 21 with the N-hydroxysuccinimidyl ester of biotin, followed by DCC-mediated condensation with pentafluorophenol. A synthesis of N-Fmoc-D-Lys(Biofin)-OH has been reported by Jacobson et al.[16], but this method is not practical for large scale syntheses because the product is only sparingly soluble in the solvents used for the extraction step and has a yield of 47% starting from $N^\alpha$-Fmoc-D-Lys-OH compared to our overall yield of 54% for the active ester 23. In addition, only an elemental analysis (with 2.5 equiv of $H_2O$ and 0.5 equiv of DMF as solvents of crystallisation) was given as characterisation[16].

Characterisation of the pentafluorophenyl ester 23 was made difficult by its highly complex 1H NMR spectrum and the similarity of its $^{13}C$ NMR spectrum to that of the starting free acid 22. The only significant difference in the $^{13}C$ NMR spectrum of the active ester was the upfield shift of 5 ppm of the lysine α-carbonyl and the presence of some unresolved multiplets in the aromatic region due to the pentafluorophenyl group. To provide more conclusive evidence for the structures of both the free acid 22 and the active ester 23, a double quantum filtered homonuclear shift correlation experiment in the phase-sensitive mode of data accumulation (DQFPh COSY) was performed on 22, and a heteronuclear multiple bond connectivity (HMBC) experiment was undertaken on 23. The cross-peaks in the COSY spectrum of biotinylated lysine 22 were sufficiently well-resolved to provide unequivocal assignments of all multiplets in the 1-dimensional $^1H$ NMR spectrum, even for resonances in the crowded methylene region. The HMBC spectrum of the active ester 23 showed strong connectivities between all the carbonyls and their adjacent protons except for the resonance at δ169.2, which was tentatively assigned to the α-carbonyl. This had no correlation to any protons under these particular experimental conditions. However, by providing unambiguous assignments for three out of the four resonances in the carbonyl region, the HMBC experiment indirectly confirmed that the resonance at δ169.2 was due to the lysine α-carbonyl, and also confirmed the assignment of the remaining resonances which were basically the addition of the spectra of N-Fmoc-L-Lys-OH and biotin17. In addition, the IR spectrum of 23 has a band of 1787cm$^{-1}$ corresponding to the ester carbonyl, a significant shift from the carboxylic acid band of 22 at 1702cm$^{-1}$.

EXAMPLE 4

Synthesis of the Oligonucleotide-Polyamide Conjugate

The model compound 5 was initially synthesised to test the efficacy of these types of conjugates as PCR primers. The polyamide moiety of this conjugate contains a 6-aminohexanoic acid residue as a spacer (Scheme I in FIG. 2), in ε-biotinylated lysine residue for detection of the PCR amplification products, and an alanine residue as a reference amino acid. The oligonucleotide moiety was a 23mer which amplifies a 700 base-pair region of the DNA of λ phage; the template is provided with the standard Cetus PCR kit for control reactions.

As with the synthesis of conjugates we have previously described[2,15], the polyamide part of the present conjugate was synthesised first on the derivatised solid support described above, by the conventional Fmoc strategy[9] since peptide synthesis conditions are harsher above, by the conventional Fmoc strategy9 since peptide synthesis conditions are harsher than those of DNA synthesis. The pendant amino and 5'-hydroxyl groups of the derivatized solid supports 18 and 19 were deprotected by treatment with 90% TFA/ethanedithiol and 3% DCA/CH$_2$Cl$_2$ respectively and then neutralised with 20% triethylamine/CH$_2$Cl$_2$. They were then subjected to a double (45 minute each) coupling with a 1:1 mixture of N-Fmoc-6-aminohexanoic acid pentafluorophenyl ester (Fmoc-εAhz-OPfp) and 1-hydroxybenzotriazole (HOBT) (2.5 molar equiv. of each). The qualitative trinitrobenzenesulfonic acid test[18] showed only trace amounts of free amino acids at the end of the first coupling and no free amino groups after the repeat coupling. Reprotection of the 5'-hydroxyl was achieved by tritylation with 4,4'-dimethoxytritylchloride in pyridine (without DMP as catalyst because of the presence of the Fmoc group) to give resin 20. The trityl loading of the resin after two successive 24 hour treatment was comparable to the nucleoside loading determined prior to the acylation reaction, confirming that the acylation had occurred with a high degree of selectivity at the pendant amine. Any remaining free carboxylic acid and amino groups were blocked as already described.

The biotinylated lysine synthon 23 and Fmoc-Ala-OPfp were coupled to solid support 20 (Scheme III) using standard Fmoc chemistry with a 5-fold excess of amino acid active ester and HOBT. The coupling efficiency of 23 was similar to that of the standard alanine derivative, the reaction being complete in one hour. Amino-acid analysis of the solid support at this stage gave the expected ratio of lysine to alanine, with loadings of 26 and 23 μmol/g for lysine and alanine respectively. The Fmoc group of alanine was removed with 20% piperidine/DMF and the resulting free amino group acetylated by treatment with Ac$_2$O/DMAP.

Following the synthesis of the polyamide, the 5'-hydroxyl of the resin-bound nucleoside was deprotected by detritylation with 3% DCA/CH$_2$Cl$_2$, and an oligonucleotide was synthesised using standard β-cyanoethyl phosphoramidite chemistry[2,10,19]. The repetitive coupling yields of oigonucleotide as assessed by trityl assays was comparable with that of DNA synthesis using normal solid supports. Cleavage from the solid support, phosphate and base deprotection by ammonia treatment[2,10,12] gave a material which was shown to be composed of two major products by polyacrylamide gel electrophoresis (PAGE). The product with the higher electrophoretic mobility contained no peptidic material while the slower-moving one contained the desired composition of amino acids. Purification by preparative PAGE resulted in high yields of the desired conjugate.

The oligonucleotide-polyamide conjugate 5 was characterised by UV spectroscopy, amino-acid analysis, nuclease digestion to its component nucleotides and PAGE. Quantitation of the oligonucleotide moiety by its UV absorbance and quantitation of the polyamide moiety by amino acid analysis gave a 1.2:1 ration of oligonucleotide to polyamide. In addition, the reactions of the amino acids were as expected, suggesting that the polyamide moiety was intact and was stable to oligonucleotide synthesis conditions. The conjugate was also 5'-end labelled with a radioactive phosphate by γ-[$^{32}$P]-ATP and T$_4$ polynucleotide kinase and analysed by PAGE with the resulting autoradiogram (FIG. 1) confirming the conjugate's homoeneity. Preliminary experiments using this conjugate as a PCR primer gave a product of the expected lengthy. Subsequent chemiluminescent detection of the biotin label in this produce showed unequivocally that the conjugate was incorporated into the PCR product as expected (data will be reported elsewhere). These types of conjugates are thus viable PCR primers.

EXAMPLE 5

PCR Analysis

The conjugate of Example 4 was dissolved in 0.1 mM EDTA solution to a final concentration of 100 ng/μL. The sequence of the oligonucleotide was GATGAGTTCGT-GTCCGTACAACT* (where T*=modified deoxyridine bearing the biotinylated triamide) which when combined with the oligonucleotide primer GGTTATCGAAATCAGC-CACAGCG was used to amplify the 500 bp region 7131–7630 of c1857 DNA from the bacteriophage λ., provided with the Perkin-Elmer PCR test kit. The normal oligonucleotide primer (with the 3'-nucleotide being a T) was also synthesized and purified in the manner described above.

Each PCR reaction mixture contained the following: 5 μL of Taq polymerase solution (2.5 U, in Taq polymerase buffer/50% glycerol), 1 μL of each oligonucleotide primer (100 ng was made up to 50 μL with autoclaved, distilled water and a drop of autoclaved mineral oil was added. All reactions were performed on a Perkin Elmer Cetus DNA Thermal Cycler instrument, using the following cycle: 95° C. (1 min), 55° C. (1 min), 72° C. (1 min), 30 cycles, ending with a 10 min step at 72° C. to ensure complete chain elongation. Gel electrophoresis of the PCR reaction mixtures (5 μL) was carried out on an agarose gel (1.5% agarose, 0.001% Ethidium Bromide), with 1 x TBE buffer, at 80 V for 1 h. The agarose gel was blotted onto a nylon membrane by the Southern procedure. The membrane was then probed for the presence of biotin by using the PHOTOGENE kit from BRL. Like Technologies Inc.. This detection is carried out in the following manner.

After soaking the membrane in Tris-buffered saline (TBS Tween 20) and then blocking in 3% bovine serum albumin in the same buffer, the membrane was incubated for 10 min with a solution of the streptavidin-alkaline phosphatase conjugate (1 mg/mL in 3M NaCl. 1 mM MgCl$_2$.0.1 mM ZnCl$_2$. 30 mM triethanolamine (pH 7.6)) diluted 1:1000 with TBS Tween 20. After washing the membrane with TBS Tween 20 for 15 min and 'Final Washer Buffer' (diluted 1:10 with distilled water) for 60 min at room temperature, the membrane was blotted to remove excess buffer. It was then placed in a development folder and treated with the chemiluminescent substrate for alkaline phosphatase supplied by the manufacturer. The membrane was stored in the dark for 3 h after which time an X-ray film was placed on top. A strong signal was recorded after a 30 sec exposure.

The UV visualization of the ethidium bromide-stained gel showed quite clearly that the PCR using the conjugate as one of the primers gave comparable amounts of amplified DNA to that performed using only normal oligonucleotide primers. Both PCR products were of the expected length.

To prove unequivocally that the amplification products are due to the biotinylated conjugate, the products on the agarose gel were blotted into nylon membrane as described above. This detection system basically involves the reaction of immobilized biotinylated DNA with a streptavidin-alkaline phosphatase conjugate which in turn catalyses a dephosphorylation reaction which results in chemiluminescence. The chemiluminescence is detected by exposure of the blot to normal X-ray film. As expected, there was only one band which contained biotin, corresponding to the PCR products arising from the biotinylated conjugate PCR primer. This shows unequivocally that the biotinylated primer was effectively incorporated into the final amplification products.

Chemiluminescent detection, even of only one biotin in this case, in extremely sensitive. A strong signal resulted after only 30 sec of exposure time, and there was signal saturation after 5 min.

REFERENCES:

The following references are incorporated herein in their entirety:
1. Becker, J. M.; Wilchek, M., Katchaliski, E., *Proc. Nall. A cad. Sci USA* 1971, 68. 2604–7.
2. Haralambidis, J.; Duncan, L.; Angus, K.; Tregear, G. W. *Nucleic Acids Research* 1990, 18, 493–499.
3. Haralambidis, J.; Chai, M.; Tregear, G.; *Nucleic Acids Research* 1987, 15, 4857–4876.
4. Damha, M. J.; Giannaris, P. A.; Zabarylo, S. V., *Nucleic Acids Research* 1990, 18, 3813–3821.
5. Penschow, J. P.; Haralambidis, J.; Aldred, P.; Tregear, G. W.; Coghlan, J. P., *Methods in Enzymology,* 1986, 124, 534–548.
6. Sarin, V. K.; Kent, B. H.; Tarn, J. P.; Merrifield, R. B., *Analytical Biochemistry,* 1981, 117, 147–157; Applied Biosystems Inc. Model 430A Peptide Synthesizer User's Manual, Version 1.3B, pp. 7–85 to 7–86, July, 1988.
7. Milligen 9050 PepSynthesizer Technical Note 3.10, Millipore Corporation, 1987.
8. Hobbs Jr., F. W. *J Org. Chem.,* 1989, 54, 3420–3422.
9. Atherton, E.; Sheppard, R. C., *Solid Phase Peptide Synthesis—a practical approach,* IRL Press: Oxford, 1989.
10. Atkinson, T.; Smith, M. In *Oligonucleotide Synthesis: A Practical Approach;* Gait, M. J. Ed.; IRL Press: Oxford, 1984; pp 35–81; Adams, S. P., Kavka, K. S.; Wykes, E. J.; Holder, S. B.; Gallupi, G. R. *J Am. Chem Soc.* 1983, 105, 661–663.
11. Pon, R. T.; Usman, N.; Ogilvie, K. K. *Bio Techniques* 1988, 6, 768–775.
12. Matteucci, M. D.; Caruthers, M. H. *J. Am. Chem. Soc.* 1981, 103, 3185–3191; Haralarnbidis, J., *PhD Thesis,* University of Melbourne, 1984.
13. Gait, M. J. *Oligonucleotide Synthesis: A Practical Approach;* IRL Press: Oxford, 1984.
14. Tong, G. unpublished results.
15. Haralarnbidis, J.; Angus, K.; Pownall, S.; Duncan, L.; Chai, M.; Tregear, G. W. *Nucleic Acids Research* 1990, 18, 501–505.
16. Jacobson, K. A.; Ukena, D.; Padgett, W.; Kirk, K. L.; Daly, J. W. *Biochemical Pharmacology* 1987, 36, 1697–1707.
17. Ikura, M.;, Kunio, H., Organic Magnetic Resonance 1982, 20, 266–273.
18. Benjamin, D. M.; McCormack, J. J.; Gump, D. W., *Analytical Chemistry* 1973, 45, 1531–1534.
19. Beaucage, S. L.; Caruthers, M. H., Tetrohedron Lett. 1981, 22, 1859–1862.

We claim:

1. A nucleotide polymer conjugate of the formula (I)

$$\text{Nu—NUC—C}=\text{C—X}^1\text{—NH—X}^2\text{—X}^3 \qquad (I)$$

where, $X^1$ is an unsubstituted or substituted $C_1$–$C_{10}$ alkylene group, in which one or more carbons may optionally be replaced by —NH—, —O— or —S—, $X^2$ is a bond, or an unsubstituted or substituted $C_1$–$C_{20}$ alkylene group, in which one or more carbons may optionally be replaced by —NH—, —O— or —S—, the optional substituents in $X^1$ or $X^2$ are selected from one or more of oxo, amino, thioxo, hydroxyl, mercapto, carboxyl, halogen, lower alkyl, phenyl, amino-lower alkyl, ester-lower alkyl, amido-lower alkyl, ether-lower alkyl, or thioether-lower alkyl, groups, the sulfur analogues of these substituents, or the side-chain substituents from naturally occurring amino acids, and the closely related analogues of these sidechains, $X^3$ is an amino acid, or a polyamide linked via its carboxy terminus, NUC is a nucleoside group of any one of the formulas:

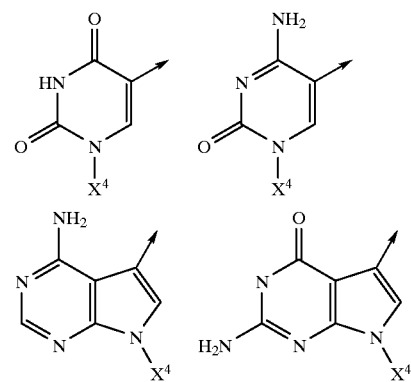

where→indicates the bond to the —C≡C— group in formula (I), and $X^4$ is a sugar group of the formula:

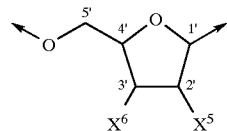

where the 5' oxygen is linked to Nu, and $X^5$ and $X^6$ are each independently, H or OR, where R is H, a protecting group, or a solid phase matrix, and Nu is an oligonucleotide.

2. The conjugate according to claim 1, where $X^1$ is $C_1$–$C_3$ alkylene, $X^2$ is —CO—($C_1$ to $C_9$ alkylene)—NH—, $X^3$ is a peptide bound through its carboxy terminus, NUC is a nucleoside of the formula:

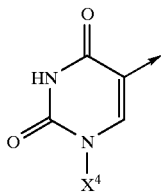

where $X^4$, $X^5$ and $X^6$ are as defined in claim 1, and Nu has the formula:

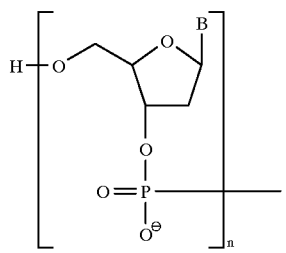

where B is independently selected from adenyl, guanyl, thyminyl or cytosinyl, and n is from 1 to about 400.

3. The conjugate according to claim 2, wherein $X^1$ is methylene, and $X^2$ is —CO—(CH$_2$)$_5$—NH—.

4. The conjugate according to claim 1, which has the formula;

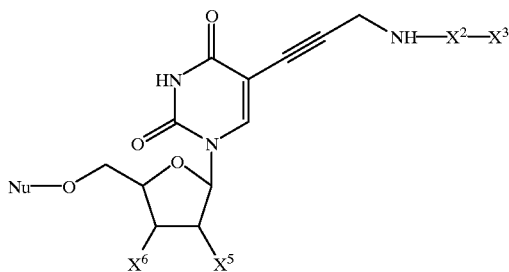

(II)

where $X^2$, $X^3$, $X^5$, $X^6$ and Nu are as defined in claim 1.

5. The conjugate according to claim 1, wherein $X^3$ is a peptide comprising from 2 to 100 amino acids.

6. The conjugate according to claim 1, wherein $X^3$ is a polyamide chain containing one or more reporter groups.

7. The conjugate according to claim 6, wherein said reporter groups are attached to said chain via the ε-amino group on a lysine group present in said chain.

8. The conjugate according to claim 2, where in the definition of Nu, n is from 2 to about 200.

9. The conjugate according to claim 1, wherein $X^5$ is H, and $X^6$ is OR, where R is H or a solid phase matrix.

10. The conjugate according to claim 1, wherein R is a solid phase matrix selected from a controlled pore glass, or a polystyrene resin.

11. A process for preparing a nucleotide polymer conjugate of the formula (I)

(I)

where, $X^1$ is an unsubstituted or substituted $C_1$–$C_{30}$ alkylene group, in which one or more carbons may optionally be replaced by —NH—, —O— or —S—, $X^2$ is a bond, or an unsubstituted or substituted $C_1$–$C_{30}$ alkylene group, in which one or more carbons may optionally be replaced by —NH—, —O— or —S—, the optional substituents in $X^1$ or $X^2$ are selected from one or more of oxo, amino, thioxo, hydroxyl, mercapto, carboxyl, halogen, lower alkyl, phenyl, amino-lower alkyl, ester-lower alkyl, amido-lower alkyl, ether-lower alkyl or thioether-lower alkyl, groups, the sulfur analogues of these substituents, or the side-chain substituents from naturally occurring amino acids, and the closely related analogues of these sidechains, $X^3$ is an amino acid, or a polyamide linked via its carboxy terminus, NUC is a nucleoside of any one of the formulas:

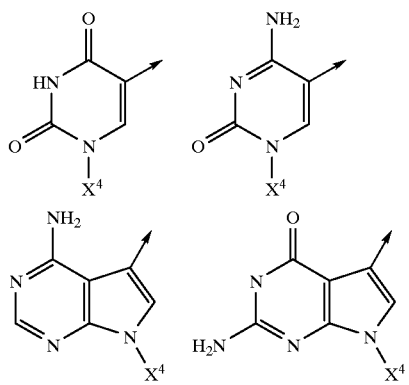

where →indicates the bond to the —C≡C— group in formula (I), and $X^4$ is a sugar group of the formula:

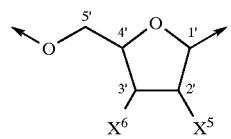

where the 5' oxygen is linked to Nu, and $X^5$ and $X^6$ are each independently, H or OR, where R is H, a protecting group, or a solid phase matrix, and Nu is a oligonucleotide, which process comprises:

(1) providing a compound of the formula (m):

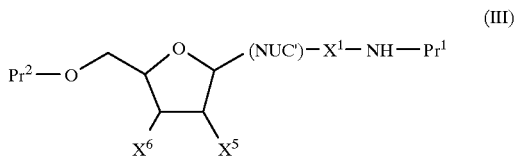

(III)

in which, NUC' is a group of any one of the following formulas:

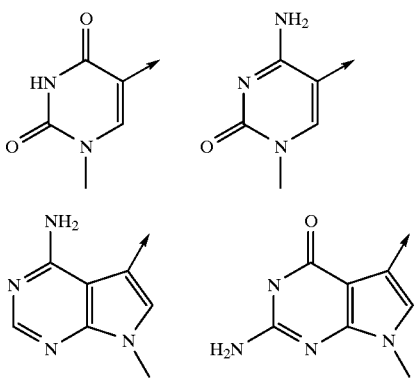

and $X^1$, $X^5$, and $X^6$ are as previously described, and $Pr^1$ and $Pr^2$ are protecting groups which may be the same or different;

(2) deprotecting the pendant amino group by removing $Pr^1$ in compound (m) under conditions which may or may not remove $Pr^2$ and thereafter reacting the deprotected compound with a compound of the formula $Pr^3XR^x$ wherein $X^2$ is as previously described, $Pr^3$ is a protecting group and $R^x$ is a leaving group, so as to covalently link $X^2$ to the pendant amino group, to give:

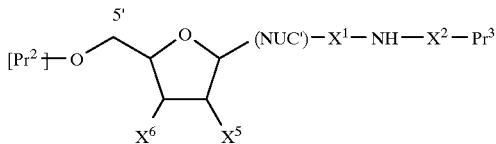

and in the case where the 5'-OH group is free this group is optionally reprotected with $Pr^2a$ removable protecting group, the same or different to $Pr^2$ in step (1), or when $X^2$ is a bond omitting step (2);

(3) deprotecting the pendant amino group by removing $Pr^3$, or $Pr^1$ when $X^1$ is a bond, in the compound of step (2) and reacting it with an activated amino acid or polyamide, to introduce all or part of $X^3$, and if only part of $X^3$ has been introduced, thereafter sequentially adding one or more activated amino acids or polyamides one or more times under standard peptide synthesis conditions to add the remainder of $X^3$ to the compound, to form:

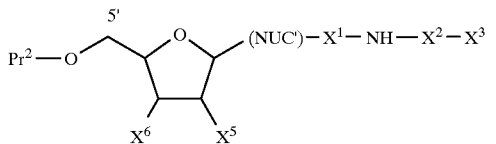

(4) deprotecting the 5'-OH group of the sugar moiety of the compound of step (3) if not previously deprotected and reacting the deprotected OH group with an activated nucleotide or oligonucleotide to form a 5'–3' bond, and thereafter sequentially adding one or more activated nucleotides to form an oligonucleotide chain, to add Nu to the compound; and (5) optionally removing any remaining protecting groups, and optionally cleaving said compound from a solid phase matrix where $X^5$ or $X^6$ is OR and R is a solid phase matrix, to give said conjugate of the Formula (I).

12. A process for preparing a nucleotide polymer conjugate of the formula:

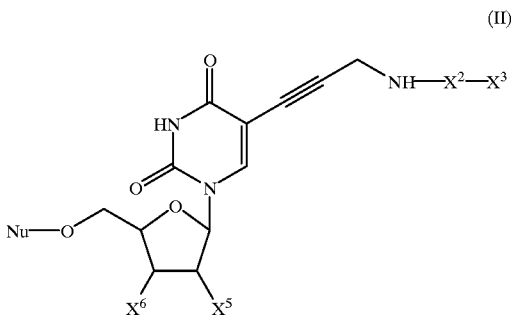

(II)

$X^2$ is a bond, or an unsubstituted or substituted $C_1$–$C_{20}$ alkylene group, in which one or more carbons may optionally be replaced by —NH—, —O— or —S—, the optional substituents in $X^2$ are selected from one or more of oxo, amino, thioxo, hydroxyl, mercapto, carboxyl, halogen, lower alkyl, phenyl, amino-lower alkyl, ester-lower alkyl, amido-lower alkyl, ether-lower alkyl, or thioether-lower alkyl groups, the sulfur analogues of those substituents, or the side-chain substituents from naturally occurring amino acids, and the closely related analogues of these sidechains, $X^3$ is an amino acid, or a polyamide linked via its carboxy terminus, $X^5$ and $X^6$ are each independently, H or OR, where R is H, a protecting group, or a solid phase matrix, and Nu is an oligonucleotide, which process comprises:

(1) providing a compound of the formula (IIIa):

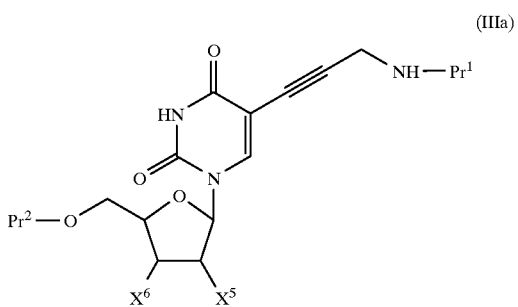

(IIIa)

in which, $X^5$ and $X^6$ are as previously described, and $Pr^1$ and $Pr^2$ are protecting groups which may be the same or different;

(2) deprotecting the pendant amino group by removing $Pr^1$ in compound (IIIa) under conditions which may or may not remove $Pr^2$ and thereafter reacting the deprotected compound with an amino acid of the formula $Pr^3X^2R^x$ wherein $X^2$ is as previously described, $Pr^3$ is a protecting group and $R^x$ is a leaving group, so as to covalently link $X^2$ to the pendant amino group, and in the case where the 5'-OH group is free this group is optionally reprotected with a removable protecting group which may be the same as or different from the protecting group $Pr^2$ in step (1), or when $X^2$ is a bond omitting step (2);

(3) deprotecting the pendent amino group by removing $Pr^3$, or $Pr^1$ when $X^2$ is a bond, in the compound of step (2) and reacting it with an activated amino acid or polyamide, to introduce all or part of $X^3$, and if only part of $X^3$ has been introduced, thereafter sequentially adding one or more activated amino acids or polyamides one or more times under standard peptide synthesis conditions to add the remainder of $X^3$ to the compound;

(4) deprotecting the 5'-OH group of the sugar moiety of the compound of step (3), if not previously deprotected, and reacting the deprotected OH group with an activated nucleotide or oligonucleotide to form a 5'–3' bond, and thereafter sequentially adding one or more activated nucleotides to form an oligonucleotide chain, to add Nu to the compound; and (5) optionally removing any remaining protecting groups, and optionally cleaving said compound from a solid phase matrix where $X^5$ and $X^6$ is OR and R is said solid phase matrix, to give said conjugate of the formula (II).

13. A method for determining the presence and location in animal or plant tissue of a specific polynucleotide population which comprises:

(a) preparing a section of the tissue to be examined;

(b) hybridizing the tissue section with an oligonucleotide polymer conjugate according to claim 1, wherein the oligonucleotide portion of the conjugate is complementary to a portion of a target polynucleotide;

(c) removing unhybridized probe material from the tissue section; and (d) detecting or identifying the locations in the tissue section where labelling by hybridization of the conjugate has occurred.

14. A method for detecting a polynucleotide immobilized to or otherwise associated with a support matrix, said method comprising contacting the support matrix with an oligonucleotide polymer conjugate according to claim 1, wherein the oligonucleotide portion of the conjugate is complementary to a portion of the target polynucleotide, and thereafter detecting hybridization of the conjugate to the support matrix.

15. A method for detecting the presence or absence of a specific viral, bacterial or other polynucleotide in a biological sample, comprising contacting the nucleic acids of the sample with an oligonucleotide polymer conjugate according to claim I which is complementary to a portion of a target polynucleotide, and thereafter detecting whether hybridization of the conjugate has occurred.

16. A diagnostic kit for detecting a desired polynucleotide, which comprises an oligonucleotide polymer conjugate according to claim 1, wherein the oligonucleotide portion of the conjugate is complementary to a portion of the desired polynucleotide; and reagents for detecting hybridization of the conjugate.

17. A diagnostic kit according to claim 16 for use in determination of the presence and location in animal or plant tissue of a specific polynucleotide population, which additionally comprises reagents for tissue section preparation.

18. A method for extending a DNA sequence which comprises reacting a conjugate according to claim 1 with nucleotide triphosphates in the presence of DNA or RNA polymerase.

19. A method of amplifying a target DNA or RNA sequence which comprises hybridizing a conjugate according to claim 1 to a target sequence to give a hybridized duplex, incubating the hybridized duplex with DNA polymerase in the presence of nucleotide triphosphate so as to copy the nucleotide sequence of the target sequence, separating the duplex by heat application, and repeating this sequence a plurality of times so as to amplify the number of copies of the target sequence.

* * * * *